US008889772B2

(12) United States Patent
Hill et al.

(10) Patent No.: US 8,889,772 B2
(45) Date of Patent: *Nov. 18, 2014

(54) METHOD FOR PRODUCING MIXTURES OF ALKYLPHOSPHONOUS ACID SALTS AND DIALKYLPHOSPHINIC ACID SALTS

(75) Inventors: Michael Hill, Hamburg (DE); Sebastian Hoerold, Diedorf (DE); Werner Krause, Huerth (DE); Martin Sicken, Cologne (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 13/643,899

(22) PCT Filed: Apr. 20, 2011

(86) PCT No.: PCT/EP2011/002014
§ 371 (c)(1),
(2), (4) Date: Nov. 13, 2012

(87) PCT Pub. No.: WO2011/134620
PCT Pub. Date: Nov. 3, 2011

(65) Prior Publication Data
US 2013/0131239 A1 May 23, 2013

(30) Foreign Application Priority Data
Apr. 29, 2010 (DE) .......................... 10 2010 018 684

(51) Int. Cl.
C08K 5/5313 (2006.01)
C09K 21/12 (2006.01)
C07F 9/48 (2006.01)
C07F 9/38 (2006.01)

(52) U.S. Cl.
CPC .............. C09K 21/12 (2013.01); C07F 9/4816 (2013.01); C07F 9/3808 (2013.01)
USPC .......................................... 524/126; 524/133

(58) Field of Classification Search
USPC .................................................. 524/126, 133
See application file for complete search history.

(56) References Cited

U.S. PATENT DOCUMENTS

| | | | |
|---|---|---|---|
| 3,900,444 A | 8/1975 | Racky et al. | |
| 4,036,811 A | 7/1977 | Noetzel et al. | |
| 5,891,226 A | 4/1999 | Kleiner et al. | |
| 6,013,707 A | 1/2000 | Kleiner et al. | |
| 6,121,445 A | 9/2000 | Suzuki et al. | |
| 6,136,973 A | 10/2000 | Suzuki et al. | |
| 6,207,736 B1 | 3/2001 | Nass et al. | |
| 6,365,071 B1 | 4/2002 | Jenewein et al. | |
| 6,509,401 B1 | 1/2003 | Jenewein et al. | |
| 6,815,558 B1 | 11/2004 | Weferling | |
| 7,049,463 B2 | 5/2006 | Wo et al. | |
| 7,420,007 B2 | 9/2008 | Bauer et al. | |
| 7,572,931 B2 | 8/2009 | Liu et al. | |
| 7,635,785 B2 | 12/2009 | Bauer et al. | |
| 2005/0137418 A1* | 6/2005 | Bauer et al. ....................... 562/8 |
| 2006/0074157 A1* | 4/2006 | Bauer et al. ................... 524/115 |
| 2006/0089435 A1 | 4/2006 | Hoerold et al. | |
| 2010/0076132 A1* | 3/2010 | Levchik et al. ............... 524/133 |
| 2013/0126805 A1 | 5/2013 | Hill et al. | |
| 2013/0131235 A1 | 5/2013 | Hoerold et al. | |
| 2013/0210975 A1 | 8/2013 | Hoerold et al. | |

FOREIGN PATENT DOCUMENTS

| | | |
|---|---|---|
| DE | 2252258 | 5/1974 |
| DE | 2447727 | 4/1976 |
| DE | 19614424 | 10/1997 |
| DE | 19734437 | 2/1999 |
| DE | 19737727 | 7/1999 |
| EP | 0794189 | 9/1997 |
| EP | PCT/EP97/01664 | 10/1997 |
| EP | 0699708 | 3/1998 |
| EP | 1055681 | 11/2000 |
| EP | 1544205 | 6/2005 |
| EP | 1544206 | 6/2005 |
| WO | WO 98/39306 | 9/1988 |
| WO | WO 96/16948 | 6/1996 |
| WO | WO 2005/105818 | 11/2005 |
| WO | PCT/US2006/045770 | 6/2007 |
| WO | WO 2007/064748 | * 6/2007 |

OTHER PUBLICATIONS

PCT international Search Report for PCT/EP2011/002014, mailed Feb. 1, 2012
English translation of the PCT International Preliminary Report on Patentability for PCT/EP2011/002014, Oct. 30, 2012.
Office Action for U.S. Appl. No. 13/643,810, mailed Mar. 5, 2014.
Office Action for U.S. Appl. No. 13/643,784, mailed Sep. 23, 2013.

* cited by examiner

Primary Examiner — Peter Szekely
(74) Attorney, Agent, or Firm — Anthony A. Bisulca

(57) ABSTRACT

The invention relates to a method for producing mixtures of alkylphosphonous acid and dialkylphosphinic acid salts, characterized in that a) a phosphinic acid source (I) is reacted with olefins (II) in the presence of a catalyst A to obtain a mixture of alkylphosphonous acid (III) and dialkylphosphinic acid (IV) or salts or esters thereof, and b) the thus obtained mixture of alkylphosphonous acid (III) and dialkylphosphinic acid (IV) or the salts or esters thereof is reacted with metal compounds of Mg, Ca, Al, Sb, Sn, Ge, Ti, Fe, Zr, Zn, Ce, Bi, Sr, Mn, Li, Na, K and/or a protonated nitrogen base to obtain the corresponding mixtures of alkylphosphonous acid salt (V) and dialkylphosphinic acid salt (VI) of said metals and/or a nitrogen compound, (V) (VI), wherein Y represents Mg, Ca, Al, Sb, Sn, Ge, Ti, Fe, Zr, Zn, Ce, Bi, Sr, Mn, Li, Na; K and/or a nitrogen compound and n represents $\frac{1}{4}$, $\frac{1}{3}$, $\frac{1}{2}$, 1.

10 Claims, No Drawings

METHOD FOR PRODUCING MIXTURES OF ALKYLPHOSPHONOUS ACID SALTS AND DIALKYLPHOSPHINIC ACID SALTS

The invention relates to a process for preparing mixtures of alkylphosphonous salts and dialkylphosphinic salts of these mixtures.

Flame retardancy can be achieved in polyesters and polyamides, for example, by addition of various additives. Normally, halogenated compounds and especially polybrominated aromatic compounds are used as flame-retardant additives. For some years, however, these halogenated flame retardants have been the subject of close attention due to environmental concerns, and so industry is now coming under increasing pressure to switch to more environmentally friendly flame-retardant additives.

Phosphorus-based products are the replacement for halogenated flame retardants. In some applications, the phosphorus-based additives exhibit a flame retardancy just as high as the halogenated equivalents thereof.

For thermoplastic polymers, the salts of phosphinic acids (phosphinates) have been found to be effective flame-retardant additives (DE-A-2 252 258 and DE-A-2 447 727). Calcium phosphinates and aluminum phosphinates have been described as particularly effective in polyesters and impair the material properties of the polymer molding compositions to a lesser degree than, for example, the alkali metal salts (EP-A-0 699 708).

In addition, synergistic combinations of phosphinates with particular nitrogen-containing compounds have been found, and these have been found to be more effective as flame retardants in a whole series of polymers than the phosphinates alone (PCT/EP97/01664, and also DE-A-197 34 437 and DE-A-197 37 727).

Salts of alkylphosphonous acids, especially phenyl- and methylphosphonous acid aluminum salt, are known to be effective flame-retardant additives in polyester (EP-A-0 794 189).

PCT/US2006/045770 describes flame-retardant thermoplastic polymers which comprise a mixture of metal salts of dialkylphosphinic acids and alkylphosphonous acids. However, by the method described therein, it is only possible to prepare the corresponding isobutyl salts.

It is therefore an object of the invention to provide a process for preparing mixtures of alkylphosphonous salts and dialkylphosphinic salts, in which the desired mixtures of alkylphosphonous salts and dialkylphosphinic salts can be prepared in a particularly simple and economically viable manner and in correspondingly high yields. Especially mixtures of alkylphosphonous salts and dialkylphosphinic salts with short side chains are to be preparable reproducibly without troublesome halogen compounds as reactants and with good yields.

This object is achieved by a process for preparing mixtures of alkylphosphonous salts and dialkylphosphinic salts, which comprises
a) reacting a phosphinic acid source (I)

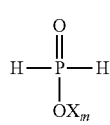

with olefins (II)

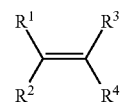

in the presence of a catalyst C to give a mixture of alkylphosphonous acid (III) and dialkylphosphinic acid (IV) or salts or esters thereof

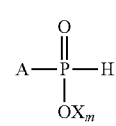

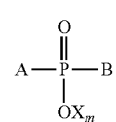

where $R^1$, $R^2$, $R^3$, $R^4$ are each independently H, $C_6$-$C_{18}$-aryl, $C_7$-$C_{18}$-arylalkyl and/or $C_7$-$C_{18}$-alkylaryl and A and B are the same or different and are each independently $C_2$-$C_{20}$-alkyl and/or $C_8$-$C_{20}$-alkylaryl and X is H, $C_1$-$C_{18}$-alkyl, $C_6$-$C_{18}$-aryl, $C_7$-$C_{18}$-arylalkyl, $C_7$-$C_{18}$-alkylaryl, $C_2$-$C_{18}$-alkenyl, $(CH_2)_kOH$, $CH_2$—$CHOH$—$CH_2OH$, $(CH_2$—$CH_2O)_kH$ or $(CH_2$—$CH_2O)_k$-alkyl, where k is an integer from 0 to 10, and/or X is H, Mg, Ca, Ba, Al, Pb, Fe, Zn, Mn, Ni, Li, Na, K and/or a protonated nitrogen base, where m is ⅓, ½, 1, and the catalyst C is a free-radical initiator and b) reacting the mixture of alkylphosphonous acid (III) and dialkylphosphinic acid (IV) or salts or esters thereof thus formed with metal compounds of Mg, Ca, Al, Sb, Sn, Ge, Ti, Fe, Zr, Zn, Ce, Bi, Sr, Mn, Li, Na, K and/or a protonated nitrogen base to give the corresponding mixtures of alkylphosphonous salt (V) and dialkylphosphinic salt (VI) of these metals and/or a nitrogen compound

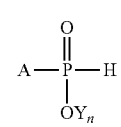

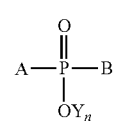

where A and B are each as defined under a) and Y is Mg, Ca, Al, Sb, Sn, Ge, Ti, Fe, Zr, Zn, Ce, Bi, Sr, Mn, Li, Na, K and/or a nitrogen compound and n is ¼, ⅓, ½, 1.

Preferably, $R^1$, $R^2$, $R^3$, $R^4$ are the same or different and are each independently H, methyl, ethyl, n-propyl, isopropyl, n-butyl, isobutyl, tert-butyl, trimethylene and/or tetramethylene.

Preferably, the olefins (II) are ethylene, 1-propylene, 1-butene, 1-pentene, cyclopentene, 1-hexene and/or cyclohexene.

Preferably, the phosphinic acid source (I) is phosphinic acid, or the sodium, potassium, calcium, magnesium, aluminum, ammonium salt and/or methyl, ethyl, propyl, i-propyl, butyl, t-butyl, glycol ester thereof.

Preferably, A and B are the same or different and are each independently ethyl, n-propyl, isopropyl, n-butyl, isobutyl, pentyl, isopentyl, cyclopentyl, hexyl, isohexyl, cyclohexyl.

The mixtures to be prepared are preferably salts of alkylphosphonous acid (V), such as aluminum(III), calcium(II), magnesium (II), cerium(III), Ti(IV) and/or zinc(II) salts of ethyl-, n-propyl-, isopropyl-, n-butyl-, isobutyl-, pentyl-, isopentyl-, cyclopentyl-, hexyl-, isohexyl- and/or cyclohexylphosphonous acid and of diethyl-, di-n-propyl-, diisopropyl-, n-propylisopropyl-, di-n-butyl-, diisobutyl-, n-butylisobutyl-, dipentyl-, diisopentyl-, n-pentylisopentyl-, dicyclopentyl-, dihexyl-, diisohexyl-, n-hexylisohexyl- and/or dicyclohexylphosphinic acid.

Preferably, the mixture of alkylphosphonous salt (V) and dialkylphosphinic salt (VI) comprises 0.5 to 35% by weight of alkylphosphonous salt (V) and 65 to 99.5% by weight of dialkylphosphinic salt (VI).

Preferably, the mixture of alkylphosphonous salt (V) and dialkylphosphinic salt (VI) comprises 3 to 30% by weight of alkylphosphonous salt (V) and 70 to 97% by weight of dialkylphosphinic salt (VI).

Preferably, the mixture of alkylphosphonous salt (V) and dialkylphosphinic salt (VI), based on the total weight of the mixture, comprises 0 to 5% by weight of further constituents such as alkylphosphonic salts and/or telomeric dialkylphosphinic salts.

The invention also relates to the use of the mixtures of alkylphosphonous salt (V) and dialkylphosphinic salt (VI) which have been prepared according to one or more of claims 1 to 9 as a flame retardant or as an intermediate for preparation of flame retardants for thermoplastic polymers, for thermoset polymers, for clearcoats, for intumescent coatings, for wood and other cellulosic products, for production of flame-retardant polymer molding compositions, for production of flame-retardant polymer moldings and/or for rendering pure and blended polyester and cellulose fabrics flame-retardant by impregnation.

Preferably, the thermoplastic polymers are polyester, polystyrene and/or polyamide, and the thermoset polymers are unsaturated polyester resins, epoxy resins, polyurethanes and/or acrylates.

The invention further relates to a flame-retardant thermoplastic or thermoset polymer molding composition comprising 2 to 50% by weight of the mixtures of alkylphosphonous salt (V) and dialkylphosphinic salt (VI) which have been prepared according to one or more of claims 1 to 9, based on the thermoplastic or thermoset polymer.

The invention additionally relates to flame-retardant thermoplastic or thermoset polymer moldings, films, filaments and fibers comprising 2 to 50% by weight of the mixtures of alkylphosphonous salt (V) and dialkylphosphinic salt (VI) which have been prepared according to one or more of claims 1 to 9, based on the thermoplastic or thermoset polymer.

The flame-retardant thermoplastic or thermoset polymer moldings, films, filaments and fibers preferably comprise 3 to 40% by weight of the mixtures of alkylphosphonous salt (V) and dialkylphosphinic salt (VI) which have been prepared according to one or more of claims 1 to 9, based on the thermoplastic or thermoset polymer.

The reactions in process stages a) and b) are preferably effected in a solvent or solvent system and in an atmosphere which comprises further gaseous constituents, for example nitrogen, oxygen, argon, carbon dioxide; the temperature is −20 to 340° C., especially 20 to 180° C., and the total pressure from 1 to 100 bar.

Preference is given to effecting the respective reaction in a solvent as a monophasic system in a homogeneous or heterogeneous mixture and/or in the gas phase.

When a polyphasic system is used, it is additionally possible to use a phase transfer catalyst.

Suitable solvents for process stages a) and b) are water, alcohols, glycols, aliphatic hydrocarbons, aromatic hydrocarbons, halohydrocarbons, alicyclic hydrocarbons, ethers, glycol ethers, ketones, esters and/or carboxylic acids.

The solvent system preferably comprises solvent system additives and water.

The solvent system preferably comprises 50 to 100% by weight of water and 0 to 50% by weight of solvent system additives, more preferably 80 to 100% by weight of water and 0 to 20% by weight of solvent system additives.

The solvent system especially comprises 95 to 100% by weight of water and 0 to 5% by weight of solvent system additives.

The solvent system additives are preferably mineral acids, acidic salts, carboxylic acids, alkalis and/or electrolytes.

The acidic salts are preferably sodium bisulfate, sodium bisulfite and/or potassium bisulfite.

The carboxylic acids are preferably formic acid, acetic acid, propionic acid, butyric acid and/or longer-chain carboxylic acids and/or dimers, oligomers and/or polymers thereof.

Preferred solution system additives are mineral acids, for example the element-hydrogen acids, acids, oxo acids, peroxo acids and peroxo diacids of the elements of the seventh, sixth, fifth, fourth and third main groups of the Periodic Table.

Particularly preferred mineral acids are hydrofluoric acid, hydrochloric acid, perchloric acid, sulfurous acid, sulfuric acid, peroxomonosulfuric acid (Caro's acid), peroxodisulfuric acid, nitrous acid, nitric acid, phosphorous acid, phosphoric acid, pyrophosphoric acid, polyphosphoric acid, peroxomonophosphoric acid, peroxodiphosphoric acid, carbonic acid, silicic acid, boric acid, peroxoboric acid.

The products (III) and (IV) and/or (V) and (VI) and/or the olefin and/or the catalyst C and/or the reactants can be isolated as desired after process stages a) and b), by distillation or rectification, by crystallization or precipitation, by filtration or centrifugation, by adsorption or chromatography, or other known methods.

Preferably, the reactions in process stages a) and b) are effected, as desired, in absorption columns, spray towers, bubble columns, stirred tanks, trickle bed reactors, flow tubes, loop reactors and/or kneaders.

Preferably, the reaction solutions/mixtures experience a mixing intensity corresponding to a rotational Reynolds number of 1 to 1 000 000, preferably of 100 to 100 000, and vigorous mixing of the respective reactants etc. is effected with an energy input of 0.080 to 10 kW/m$^3$, preferably 0.30-1.65 kW/m$^3$.

Preference is given to effecting the reaction in process stage a) in a phosphinic acid/solvent molar ratio of 1:10 000 to 1:0, more preferably at 1:50 to 1:1.

The phosphinic acid source (I) preferably comprises phosphinic acid (hypophosphorous acid, $H_3PO_2$), a salt of phosphinic acid, an ester of phosphinic acid or mixtures thereof.

The salt of phosphinic acid (I) preferably comprises alkali metal salts, alkaline earth metal salts and/or ammonium salts.

The esters of phosphinic acid (I) are preferably alkyl, hydroxyalkyl, alkylaryl, aryl and/or alkenyl esters.

The esters of alkylphosphonous acid (II) are preferably the corresponding methyl, ethyl, propyl, i-propyl, butyl, t-butyl, glycol esters.

Y is preferably Mg, Ca, Al, Ti, Fe, Zr, Zn, Ce and/or a nitrogen compound.

When the phosphinic acid source (I) in step a) is phosphinic acid, an esterification can be conducted in order to obtain the ester (I) thereof.

When the phosphinic acid source (I) in step a) is a salt, an acidic hydrolysis can be conducted in order to obtain the free phosphinic acid (I).

When the mixture of alkylphosphonous acid (III) and dialkylphosphinic acid (IV) after step a) is an ester, it is possible to perform an acidic or basic hydrolysis in order to obtain the free alkylphosphonous acid (III) and dialkylphosphinic acid (IV) or salt thereof.

When the mixture of alkylphosphonous acid (III) and dialkylphosphinic acid (IV) after step a) is a salt, it is possible to perform an acidic hydrolysis in order to obtain the free alkylphosphonous acid (III) and dialkylphosphinic acid (IV).

Preferably, the phosphinic acid is prepared in situ from salts of phosphinic acid and at least one mineral acid, where the ratio of additive acid to hypophosphite (on the basis of equivalents) is 0:1 to 2:1.

An equivalent is the fraction of the number of moles of acid divided by the number of acidic protons.

Preferably, $R^1$, $R^2$, $R^3$, $R^4$ in the olefin (II) in process stage a) are the same or different and are each independently H, methyl, ethyl, n-propyl, isopropyl, n-butyl, isobutyl, tert-butyl.

Particular preference is given to using ethylene as the olefin.

Suitable solvents for process stages a) and b) are water, alcohols, glycols, aliphatic hydrocarbons, aromatic hydrocarbons, halohydrocarbons, alicyclic hydrocarbons, ethers, glycol ethers, ketones, esters and/or carboxylic acids.

Suitable solvents in process stage a) are also the olefins and phosphinic acid sources used. These offer advantages in the form of a higher space-time yield.

Preference is given to performing the reaction in process stage a) under the autogenous vapor pressure of the olefin and/or of the solvent.

Preference is given to effecting the reaction in process stage a) at a partial pressure of the olefin of 0.01-100 bar, more preferably at a partial pressure of the olefin of 0.1-10 bar.

The atmosphere preferably comprises gaseous components which are not involved in the reaction.

The gaseous components are preferably oxygen, nitrogen, carbon dioxide, noble gases, hydrogen and/or alkanes.

Preferably, the atmosphere in step a), in the course of the reaction, consists to an extent of 50 to 99.9% by weight of constituents of the solvent system and olefin, preferably to an extent of 70 to 95% by weight.

Preference is given to effecting the reaction in process stage a) in a phosphinic acid/olefin molar ratio of 1:10 000 to 1:0.001, more preferably in a ratio of 1:30 to 1:0.01.

In principle, suitable free-radical initiators are all systems which generate free radicals. The addition of the olefin can be initiated by an anionic initiator or free-radical initiator or by photochemical means.

Particularly preferred free-radical initiators, as used in process stage a), are peroxo compounds such as peroxomonosulfuric acid, potassium peroxomonosulfate, peroxodisulfuric acid, potassium peroxodisulfate, sodium peroxodisulfate and/or ammonium peroxodisulfate.

Particularly preferred free-radical initiators are compounds which can form peroxides in the solvent system, such as lithium peroxide, sodium peroxide, potassium peroxide, calcium peroxide, strontium peroxide, barium peroxide, magnesium peroxide and zinc peroxide, sodium peroxoborate, potassium peroxoborate, calcium peroxoborate, barium peroxoborate, strontium peroxoborate and magnesium peroxoborate and the hydrates and peroxohydrates thereof, peroxomonophosphoric acid, peroxodiphosphoric acid, potassium peroxodiphosphate, ammonium peroxodiphosphate, potassium ammonium peroxodiphosphate, ammonium triphosphate diperoxophosphate hydrate, sodium carbonate peroxohydrate, urea peroxohydrate, ammonium oxalate peroxide, sodium pyrophosphate diperoxohydrate, sodium phosphate peroxohydrate, potassium acetate peroxohydrate, sodium silicate peroxohydrate.

Preferred free-radical initiators are hydrogen peroxide, performic acid, peracetic acid, benzoyl peroxide, di-tert-butyl peroxide, dicumyl peroxide, 2,4-dichlorobenzoyl peroxide, decanoyl peroxide, lauryl peroxide, cumene hydroperoxide, pinene hydroperoxide, p-menthane hydroperoxide, tert-butyl hydroperoxide, acetylacetone peroxide, methyl ethyl ketone peroxide, succinyl peroxide, dicetyl peroxydicarbonate, tert-butyl peroxyacetate, tert-butylperoxymaleic acid, tert-butyl peroxybenzoate and/or acetylcyclohexylsulfonyl peroxide.

Preferred free-radical initiators are water-soluble azo initiators such as 2,2'-azobis[2-(2-imidazolin-2-yl)propane]dihydrochloride, 2,2'-azobis[2-(2-imidazolin-2-yl)propane] disulfate dihydrate, 2,2'-azobis(2-methylpropionamidine) dihydrochloride, 2,2'-azobis{2-[1-(2-hydroxyethyl)-2-imidazolin-2-yl]propane}dihydrochloride, 2,2'-azobis[N-(2-carboxyethyl)-2-methylpropionamidine]hydrate, 2,2'-azobis[2-(2-imidazolin-2-yl)propane], 2,2'-azobis(1-imino-1-pyrrolidino-2-ethylpropane)dihydrochloride, 2,2'-azobis{2-methyl-N-[1,1-bis(hydroxymethyl)-2-hydroxyethyl] propionamide, 2,2'-azobis[2-methyl-N-(2-hydroxyethyl) propionamide], 4,4'-azobis(4-cyanopentanoic acid).

Preference is given to azo initiators such as 2,2'-azobis(2,4-dimethylvaleronitrile), azobis(isobutyronitrile), 2,2'-azobis(2-methylbutyronitrile), 2,2'-azobis(4-methoxy-2,4-dimethylvaleronitrile), dimethyl 2,2'-azobis(2-methylpropionate),1,1'-azobis(cyclohexane-1-carbonitrile), 2,2'-azobis[N-(2-propenyl)-2-methylpropionamide], 1-[(cyano-1-methylethyl)azo]formamide, 2,2'-azobis(N-butyl-2-methylpropionamide), 2,2'-azobis(N-cyclohexyl-2-methylpropionamide), 2,2'-azobis{2-methyl-N-[2-(1-hydroxybutyl)]propionamide}, 2-tert-butylazo-2-cyanopropane, dimethyl azodiisobutyrate, 2-tert-butylazo-1-cyanocyclohexane, 1-tert-amylazo-1-cyanocyclohexane.

Additionally preferred are alkyl perketals such as 2,2-bis (tert-butylperoxy)butane, ethyl 3,3-bis(tert-butylperoxy)butyrate, 1,1-di(tert-butylperoxy)cyclohexane.

Preference is given to using the free-radical initiator in amounts of 0.05 to 5 mol %, based on the particular olefin (II).

Preference is given to using the free-radical initiator in amounts of 0.001 to 10 mol %, based on the phosphinic acid source.

Preference is given to metering in the free-radical initiator at a rate of 0.01 to 10 mol % of initiator per hour, based on the phosphorus-containing compound.

The reactions in process stages a) and b) are preferably effected in a solvent or solvent system and in an atmosphere which comprises further gaseous constituents, for example nitrogen, oxygen, argon, carbon dioxide; the temperature is −20 to 340° C., especially 20 to 180° C., and the total pressure from 1 to 100 bar.

Preference is given to effecting the respective reaction in a solvent as a monophasic system in a homogeneous or heterogeneous mixture and/or in the gas phase.

When a polyphasic system is used, it is additionally possible to use a phase transfer catalyst.

The mixture of alkylphosphonous acid (III) and dialkylphosphinic acid (IV) may, in this context, based on the total weight, comprise 0 to 10% by weight of further phosphorus-containing constituents such as alkylphosphonic salts and/or telomers.

The mixture of alkylphosphonous acid (III) and dialkylphosphinic acid (IV) is subsequently converted in process stage b) to mixtures of further metal salts of alkylphosphonous acid (V) and dialkylphosphinic acid (VI).

The metal compounds used in process stage b) are preferably compounds of the metals Mg, Ca, Al, Sb, Sn, Ge, Ti, Fe, Zr, Zn, Ce, Bi, Sr, Mn, Li, Na, K, more preferably Mg, Ca, Al, Ti, Zr, Zn, Sn, Ce, Fe.

Preferably, in process stage b), the mixture of alkylphosphonous acid (III) and dialkylphosphinic acid (IV) or esters and/or alkali metal salts thereof obtained after process stage a) is reacted with metal compounds of Mg, Ca, Al, Zn, Ti, Sn, Zr, Ce or Fe to give the mixture of alkylphosphonous salt (V) and dialkylphosphinic salt (VI) of these metals.

The reaction is effected in a molar ratio of phosphorus to metal of 8:1 to 1:3.

Preferably, the product mixture obtained after process stage a) is reacted with the metal compounds without further purification.

In a further embodiment of the process, the product mixture obtained after process stage a) is worked up.

Preference is given to working up the product mixture by isolating the mixture of alkylphosphonous acid (III) and dialkylphosphinic acid (IV) and/or alkali metal salts thereof.

Preference is given to effecting the isolation step by removing the solvent system, for example by evaporative concentration.

Preference is given to effecting the isolation step by removing the solvent system and the secondary components dissolved therein, for example by solid/liquid separation methods.

Preference is given to working up the product mixture by removing insoluble by-products, for example by solid/liquid separation methods.

Preference is given to conversion in process stage b) in a given solvent system which has been modified. For this purpose, acidic components, solubilizers, foam inhibitors etc. are added.

When the mixture of alkylphosphonous acid (III) and dialkylphosphinic acid (IV) after step a) is a mixture of the esters, it is possible with preference to perform an acidic or basic hydrolysis in order to obtain the mixture of alkylphosphonous acid (III) and dialkylphosphinic acid (IV) or salts thereof.

Preferably, mixture of alkylphosphonous ester (III) and dialkylphosphinic ester (IV) or salts thereof obtained in process stage a) is converted to the corresponding mixture of alkylphosphonous acid (III) and dialkylphosphinic acid (IV) and the latter is reacted in process stage b) with metal compounds of Mg, Ca, Al, Zn, Ti, Sn, Zr, Ce or Fe to give the mixtures of alkylphosphonous salt (V) and dialkylphosphinic salt (VI) of these metals.

Preferably, mixture of alkylphosphonous acid (III) and dialkylphosphinic acid (IV) or esters thereof obtained in process stage a) is converted to mixture of alkylphosphonous acid alkali metal salt (III) and dialkylphosphinic acid alkali metal salt (IV) and the latter is reacted in process stage b) with metal compounds of Mg, Ca, Al, Zn, Ti, Sn, Zr, Ce or Fe to give the mixtures of alkylphosphonous salt (V) and dialkylphosphinic salt (VI) of these metals.

The metal compounds of Mg, Ca, Al, Ti, Sn, Zr, Ce or Fe for process stage b) are preferably metals, metal oxides, hydroxides, oxide hydroxides, borates, carbonates, hydroxocarbonates, mixed hydroxocarbonates, phosphates, sulfates, hydroxosulfates, mixed hydroxosulfate, oxysulfates, acetates, nitrates, fluorides, chlorides, oxychlorides, bromides, iodides, carboxylic acid derivatives, for example acetate, formate, oxalate, tartrate, benzoate and/or alkoxides, for example n-propoxide, n-butoxide, tert-butoxide, isopropoxide, ethoxide and the hydrates thereof.

In the case of the aluminum compounds, preference is given to metallic aluminum and aluminum salts with anions of the seventh main group, for example aluminum fluoride, aluminum fluoride trihydrate, aluminum chloride (anhydrous, crystallizes; anhydrous, sublimes), aluminum chloride hexahydrate, aluminum hydroxychloride, ALCHLOR®-AC from Hardman Australia, basic aluminum chloride solution, aluminum chloride solution, sulfate-conditioned polyaluminum chloride solution (PACS) from Lurgi Lifescience, OBRAFLOC 18® from Oker Chemie GmbH, Alkaflock®, Ekocid® 60 products, Sachtoklar® products, Ekofloc® products, Ekozet products from Sachtleben, Locron®, Parimal® products from Clariant, anhydrous aluminum bromide, aluminum iodide, aluminum iodide hexahydrate.

Preference is given to aluminum salts with anions of the sixth main group, for example aluminum sulfide, aluminum selenide.

Preference is given to aluminum salts with anions of the fifth main group, for example aluminum phosphide, aluminum hypophosphite, aluminum antimonide, aluminum nitride, and aluminum salts with anions of the fourth main group, for example aluminum carbide, aluminum hexafluorosilicate; and likewise aluminum salts with anions of the first main group, for example aluminum hydride, aluminum calcium hydride, aluminum borohydride or else aluminum salts of the oxo acids of the seventh main group, for example aluminum chlorate.

Preference is given to aluminum salts of the oxo acids of the sixth main group, for example aluminum sulfate, aluminum sulfate hydrate, aluminum sulfate hexahydrate, aluminum sulfate hexadecasulfate, aluminum sulfate octadecasulfate, aluminum sulfate solution from Ekachemicals, aluminum sulfate liquid from Oker Chemie GmbH, sodium aluminum sulfate, sodium aluminum sulfate dodecahydrate, aluminum potassium sulfate, aluminum potassium sulfate dodecahydrate, aluminum ammonium sulfate, aluminum ammonium sulfate dodecahydrate, magaldrate ($Al_5Mg_{10}(OH)_{31}(SO_4)_2 \times nH_2O$).

Preference is also given to aluminum salts of the oxo acids of the fifth main group, for example aluminum nitrate nonahydrate, aluminum metaphosphate, aluminum phosphate, light aluminum phosphate hydrate, monobasic aluminum phosphate, monobasic aluminum phosphate solution; and likewise aluminum salts of the oxo acids of the fourth main group, for example aluminum silicate, aluminum magnesium silicate, aluminum magnesium silicate hydrate (almasilate), aluminum carbonate, hydrotalcite ($Mg_6Al_2(OH)_{16}CO_3 * nH_2O$), dihydroxyaluminum sodium carbonate, $NaAl(OH)_2CO_3$ and aluminum salts of the oxo acids of the third main group, for example aluminum borate or else aluminum salts of the pseudohalides, for example aluminum thiocyanate.

Preference is given to aluminum oxide (purum, purissum, technical, basic, neutral, acidic), aluminum oxide hydrate, aluminum hydroxide or mixed aluminum oxide hydroxide and/or polyaluminum hydroxy compounds, which preferably have an aluminum content of 9 to 40% by weight.

Preferred aluminum salts are those with organic anions, for example aluminum salts of mono-, di-, oligo-, polycarboxylic acids, for example aluminum diacetate, aluminum acetate basic, aluminum subacetate, aluminum acetotartrate, aluminum formate, aluminum lactate, aluminum oxalate, aluminum tartrate, aluminum oleate, aluminum palmitate, aluminum monostearate, aluminum stearate, aluminum trifluoromethanesulfonate, aluminum benzoate, aluminum salicylate, aluminum hexaureasulfate triiodide, aluminum 8-oxyquinolate.

In the case of the zinc compounds, preference is given to elemental metallic zinc and zinc salts with inorganic anions, for example zinc halides (zinc fluoride, zinc fluoride tetrahydrate, zinc chloride (zinc butter), bromides zinc iodide).

Preference is given to zinc salts of the oxo acids of the third main group (zinc borate, e.g. Firebrake ZB, Firebrake 415, Firebrake 500) and zinc salts of the oxo acids of the fourth main group (basic) zinc carbonate, zinc hydroxide carbonate, anhydrous zinc carbonate, basic zinc carbonate hydrate, (basic) zinc silicate, zinc hexafluorosilicate, zinc hexafluorosilicate hexahydrate, zinc stannate, zinc hydroxide stannate, zinc magnesium aluminum hydroxide carbonate) and zinc salts of the oxo acids of the fifth main group (zinc nitrate, zinc nitrate hexahydrate, zinc nitrite, zinc phosphate, zinc pyrophosphate); and likewise zinc salts of the oxo acids of the sixth main group (zinc sulfate, zinc sulfate monohydrate, zinc sulfate heptahydrate) and zinc salts of the oxo acids of the seventh main group (hypohalites, halites, halates, e.g. zinc iodate, perhalates, e.g. zinc perchlorate).

Preference is given to zinc salts of the pseudohalides (zinc thiocyanate, zinc cyanate, zinc cyanide).

Preference is given to zinc oxides, zinc peroxides (e.g. zinc peroxide), zinc hydroxides or mixed zinc oxide hydroxides (standard zinc oxide, for example from Grillo, activated zinc oxide, for example from Rheinchemie, Zincit, Calamin).

Preference is given to zinc salts of the oxo acids of the transition metals (zinc chromate(VI) hydroxide (zinc yellow), zinc chromite, zinc molybdate, e.g. Kemgard™ 911 B, zinc permanganate, zinc molybdate-magnesium silicate, e.g. Kemgard™ 911 C).

Preferred zinc salts are those with organic anions, which include zinc salts of mono-, di-, oligo-, polycarboxylic acids, salts of formic acid (zinc formates), of acetic acid (zinc acetates, zinc acetate dihydrate, galzin), of trifluoroacetic acid (zinc trifluoroacetate hydrate), zinc propionate, zinc butyrate, zinc valerate, zinc caprylate, zinc oleate, zinc stearate, of oxalic acid (zinc oxalate), of tartaric acid (zinc tartrate), citric acid (tribasic zinc citrate dihydrate), benzoic acid (benzoate), zinc salicylate, lactic acid (zinc lactate, zinc lactate trihydrate), acrylic acid, maleic acid, succinic acid, of amino acids (glycine), of acidic hydroxo functions (zinc phenoxide etc.), zinc para-phenolsulfonate, zinc para-phenolsulfonate hydrate, zinc acetylacetonate hydrate, zinc tannate, zinc dimethyldithiocarbamate, zinc trifluoromethanesulfonate.

Preference is given to zinc phosphide, zinc selenide, zinc telluride.

In the case of the titanium compounds is metallic titanium, as are titanium salts with inorganic anions, for example chloride, nitrate or sulfate ions, and organic anions, for example formate or acetate ions. Particular preference is given to titanium dichloride, titanium sesquisulfate, titanium(IV) bromide, titanium(IV) fluoride, titanium(III) chloride, titanium (IV) chloride, titanium(IV) chloride-tetrahydrofuran complex, titanium(IV) oxychloride, titanium(IV) oxychloride-hydrochloric acid solution, titanium(IV) oxysulfate, titanium(IV) oxysulfate-sulfuric acid solution, or else titanium oxides. Preferred titanium alkoxides are titanium(IV) n-propoxide (Tilcom® NPT, Vertec® NPT), titanium(IV) n-butoxide, titanium chloride triisopropoxide, titanium(IV) ethoxide, titanium(IV) 2-ethylhexyloxide (Tilcom® EHT, Vertetec® EHT)

In the case of the tin compounds, preference is given to metallic tin and tin salts (tin(II)chloride, tin(II) chloride dihydrate, tin(IV) chloride), and likewise to tin oxides and, as the preferred tin alkoxide, tin(IV) tert-butoxide.

In the case of the zirconium compounds, preference is given to metallic zirconium and zirconium salts such as zirconium(IV) chloride, zirconium sulfate, zirconium sulfate tetrahydrate, zirconyl acetate, zirconyl chloride, zirconyl chloride octahydrate. Preference is additionally given to zirconium oxides and, as the preferred zirconium alkoxide, zirconium(IV) tert-butoxide.

The metal compounds are preferably aluminum chloride, aluminum hydroxide, aluminum nitrate, aluminum sulfate, titanyl sulfate, titanium tetrabutoxide, zinc nitrate, zinc oxide, zinc hydroxide and/or zinc sulfate.

The reaction in process stage b) is effected at a solids content of the mixture of alkylphosphonous salt (V) and dialkylphosphinic salt (VI) of 0.1 to 70% by weight, preferably 5 to 40% by weight.

Preference is given to effecting the reaction in process stage b) at a temperature of 20 to 250° C., preferably at a temperature of 89 to 120° C.

Preference is given to effecting the reaction in process stage b) at a pressure between 0.01 and 1,000 bar, preferably 0.1 to 100 bar.

Preference is given to effecting the reaction in process stage b) over a reaction time of the mixtures of alkylphosphonous acid (III) and dialkylphosphinic acid (IV) and/or alkali metal salts thereof with metal compounds of Mg, Ca, Al, Zn, Ti, Zr, Ce or Fe to give the mixtures of alkylphosphonous salt (V) and dialkylphosphinic salt (VI) of these metals of $1*10^{-7}$ to $1*10^{2}$ h.

Preferably, the mixtures of alkylphosphonous salt (V) and dialkylphosphinic salt (VI) removed from the reaction mixture by filtration and/or centrifugation after process stage b) are dried.

Preferably, the mixtures of alkylphosphonous salt (V) and dialkylphosphinic salt (VI) are removed in process stage b) with pressurized suction filters, vacuum suction filters, stirred suction filters, pressurized cartridge filters, axial leaf filters, circular leaf filters, centrifugal disk filters, chamber/frame filter presses, automatic chamber filter presses, vacuum cellular drum filters, vacuum cellular disk filters, vacuum inside cell filters, vacuum pan filters, rotary pressure filters, vacuum belt filters.

Preferably, the filtration pressure is $5*10^{-6}$ to 60 bar, the filtration temperature 0 to 400° C., the specific filter performance 10 to 200 $kg*h^{-1}*m^{-2}$ and the residual moisture content of the resulting filtercake 5 to 60%.

Preferably, the mixtures of alkylphosphonous salt (V) and dialkylphosphinic salt (VI) are removed in process stage b) with fully encased centrifuges such as overflow centrifuges, peeler centrifuges, chamber centrifuges, screw conveyor centrifuges, pan centrifuges, tube centrifuges, screen centrifuges such as overdriven and pendulum centrifuges, screen-conveyor centrifuges, screen-bowl centrifuges or pusher centrifuges.

The acceleration ratio is preferably 300 to 15 000, the suspension throughput 2 to 400 $m^3*h^{-1}$, the solids throughput 5 to 80 $t*h^{-1}$ and the resulting moisture content of the resulting cake 5 to 60%.

Suitable apparatuses for the drying are chamber driers, channel driers, belt driers (air speed 2-3 m/s), pan driers (temperature 20 to 400° C.), drum driers (hot gas temperature 100-250° C.), paddle driers (temperature 50-300° C.), flow driers (air speed 10-60 m/s, air exhaust temperature 50-300° C.), fluidized bed driers (air speed 0.2-0.5 m/s, air exhaust temperature 50-300° C.), roller driers, tubular driers (temperature 20 to 200° C.), paddle driers, vacuum drying cabinets (temperature 20 to 300° C., pressure 0.001-0.016 MPa), vacuum roller driers (temperature 20 to 300° C., pressure 0.004-0.014 MPa), vacuum paddle driers (temperature 20 to 300° C., pressure 0.003-0.02 MPa), vacuum conical driers (temperature 20 to 300° C., pressure 0.003-0.02 MPa).

Preferably, the mixtures of alkylphosphonous salt (V) and dialkylphosphinic salt (VI) of the metals Mg, Ca, Al, Zn, Ti, Sn, Zr, Ce or Fe, as desired, have a residual moisture content of 0.01 to 10% by weight, preferably of 0.1 to 1% by weight, a mean particle size of 0.1 to 2000 μm, preferably of 10 to 500 μm, a bulk density of 80 to 800 g/l, preferably of 200 to 700 g/l, a Pfrengle flowability of 0.5 to 10, preferably of 1 to 5.

The mixtures of alkylphosphonous salt (V) and dialkylphosphinic salt (VI) of the metals Mg, Ca, Al, Zn, Ti, Sn, Zr, Ce or Fe may be obtained here as cocrystals and/or physical mixtures.

The mixtures of alkylphosphonous salt (V) and dialkylphosphinic salt (VI) of the metals Mg, Ca, Al, Zn, Ti, Sn, Zr, Ce or Fe here may comprise, based on the total weight of the mixture, 0 to 5% by weight of further constituents such as alkylphosphonic salts and/or telomeric dialkylphosphinic salts of the metals Mg, Ca, Al, Zn, Ti, Sn, Zr, Ce or Fe.

The invention likewise relates to a solution of mixtures of alkylphosphonous acid (III) and dialkylphosphinic acid (IV) and/or esters and/or alkali metal salts thereof which comprises 10 to 100% by weight of alkylphosphonous acid (III) and dialkylphosphinic acid (IV) and/or esters and/or alkali metal salts thereof 10 to 100% by weight of solvent system, where the total is 100% by weight.

Preference is given to mixtures of alkylphosphonous salt (V) and dialkylphosphinic salt (VI) of the metals Mg, Ca, Al, Zn, Sn, Ti, Ce, Zr or Fe which have been obtained by a process for preparing such mixtures of alkylphosphonous salt (V) and dialkylphosphinic salt (VI), in which
a) phosphinic acid and/or salts thereof are reacted with olefins in the presence of a catalyst to give mixtures of alkylphosphonous acid (III) and dialkylphosphinic acid (IV) and/or alkali metal salts thereof in a solvent system and
b) the mixtures of alkylphosphonous acid (III) and dialkylphosphinic acid (IV) and/or alkali metal or alkaline earth metal salts obtained after a) are reacted with metal compounds of Mg, Ca, Al, Zn, Ti, Ce, Zr or Fe to give the mixtures of alkylphosphonous salt (V) and dialkylphosphinic salt (VI) of these metals.

The present invention also provides, more particularly, a process in which sodium hypophosphite is reacted with ethylene in the presence of sodium peroxodisulfate in water to give the sodium salt of the mixture of alkylphosphonous acid (III) and dialkylphosphinic acid (IV) as the main product, and this product is subsequently reacted with aluminum sulfate to give the aluminum salt of the mixture of alkylphosphonous acid (V) and dialkylphosphinic acid (VI).

The present invention also provides, more particularly, a process in which phosphinic acid is reacted with ethylene in the presence of sodium peroxodisulfate in water to give the mixture of alkylphosphonous acid (III) and dialkylphosphinic acid (IV) as the main product, and this product is subsequently reacted with aluminum hydroxide to give the aluminum salt of the mixture of alkylphosphonous acid (V) and dialkylphosphinic acid (VI).

Preference is likewise given to mixtures of alkylphosphonous acid (III) and dialkylphosphinic acid (IV) and/or the alkali metal or alkaline earth metal salts thereof which have been obtained by reaction of phosphinic acid and/or salts thereof with olefins in the presence of a catalyst to give mixtures of alkylphosphonous acid (III) and dialkylphosphinic acid (IV) and/or alkali metal or alkaline earth metal salts thereof in a solvent system.

Preference is likewise given to mixtures of alkylphosphonous acid (III) and dialkylphosphinic acid (IV) and/or alkali metal or alkaline earth metal salts thereof. Which have been obtained by reaction of phosphinic acid and/or salts thereof with olefins in the presence of a catalyst to give mixtures of alkylphosphonous acid (III) and dialkylphosphinic acid (IV) and/or alkali metal salts thereof in a solvent system and subsequent conversion of the resulting mixtures of alkylphosphonous acid (III) and dialkylphosphinic acid (IV) derivatives to the other compound group in each case, in order to arrive at a uniform product.

Preference is likewise given to mixtures of alkylphosphonous salts (V) and dialkylphosphinic salts (VI) which have been obtained by reaction of
a) phosphinic acid and/or the alkali metal or alkaline earth metal salts thereof with olefins in the presence of a catalyst to give mixtures of alkylphosphonous acid (III) and dialkylphosphinic acid (IV) and/or alkali metal or alkaline earth metal salts thereof in a solvent system and then
a1) conversion of the mixtures of alkylphosphonous acid and dialkylphosphinic acid (III) and (IV) derivatives obtained after a) to the other compound group in each case, in order to arrive at a uniform product, and then
b) reaction of the mixtures of alkylphosphonous acid and dialkylphosphinic acid derivatives (III) and (IV) obtained after a1) with metal compounds of Mg, Ca, Al, Zn, Sn, Ti, Ce, Zr or Fe to give the mixtures of alkylphosphonous salts (V) and dialkylphosphinic salts (VI) of these metals.

Preference is likewise given to mixtures of alkylphosphonous salts (V) and dialkylphosphinic salts (VI) which have been obtained by conversion of mixtures of alkylphosphonous salt (III) and dialkylphosphinic salt (IV) obtained in process stage a) to the mixtures of alkylphosphonous acid (III) and dialkylphosphinic acid (IV) and subsequent reaction of these mixtures of alkylphosphonous acid (III) and dialkylphosphinic acid (IV) with metal compounds of Mg, Ca, Al, Zn, Sn, Ti, Ce, Zr or Fe to give the mixtures of alkylphosphonous salts (V) and dialkylphosphinic salts (VI) of these metals.

The present invention also provides, more particularly, a process in which sodium hypophosphite is reacted with ethylene in the presence of sodium peroxodisulfate in water to give the sodium salt of the mixture of alkylphosphonous acid (III) and dialkylphosphinic acid (IV) as the main product, and this product is subsequently converted with sulfuric acid to the mixture of alkylphosphonous acid (III) and dialkylphosphinic acid (IV) and reacted with aluminum hydroxide to give the aluminum salt of the mixture of alkylphosphonous acid (V) and dialkylphosphinic acid (VI).

The present invention also provides, more particularly, a process in which phosphinic acid is reacted with ethylene in the presence of sodium peroxodisulfate in water to give the mixture of alkylphosphonous acid (III) and dialkylphosphinic acid (IV) as the main product, and this product is subsequently converted with sodium hydroxide solution to the mixture of the sodium salt of alkylphosphonous acid (III) and dialkylphosphinic acid (IV) and reacted with aluminum sulfate to give the aluminum salt of the mixture of alkylphosphonous acid (V) and dialkylphosphinic acid (VI).

Preference is likewise given to mixtures of alkylphosphonous salts (V) and dialkylphosphinic salts (VI) which have been obtained by conversion of mixtures of alkylphosphonous acid (III) and dialkylphosphinic acid (IV) obtained in process stage a) to mixtures of alkylphosphonous salt (III) and dialkylphosphinic salt (IV) and subsequent reaction of these mixtures of alkylphosphonous salt (III) and dialkylphosphinic salt (IV) with metal compounds of Mg, Ca, Al, Zn, Sn, Ti, Ce, Zr or Fe to give the mixtures of alkylphosphonous salts (V) and dialkylphosphinic salts (VI) of these metals.

The mixtures of alkylphosphonous salt (V) and dialkylphosphinic salt (VI) prepared by the process according to the invention can be used especially as a flame retardant or as an intermediate for preparation of flame retardants.

Preferably, the mixture of alkylphosphonous salt (V) and dialkylphosphinic salt (VI) comprises 0.5 to 35% by weight of alkylphosphonous salt (V) and 65 to 99.5% by weight of dialkylphosphinic salt (VI).

Preferably, the mixture of alkylphosphonous salt (V) and dialkylphosphinic salt (VI) comprises 3 to 30% by weight of alkylphosphonous salt and 70 to 97% by weight of dialkylphosphinic salt.

Preferably, the mixture of alkylphosphonous salt (V) and dialkylphosphinic salt (VI), based on the total weight of the mixture, comprises 0 to 5% by weight of further constituents such as alkylphosphonic salts and/or telomeric dialkylphosphinic salts.

In a particular embodiment, the inventive mixture of alkylphosphonous salt (V) and dialkylphosphinic salt (VI) comprises 0.5 to 30% by weight of ethylphosphonous acid aluminum salt and 70 to 99.5% by weight of diethylphosphinic acid aluminum salt.

In addition, it is possible to add 0 to 50% by weight of at least one further flame retardant to the flame-retardant thermoplastic or thermoset polymer molding composition or to the flame-retardant thermoplastic or thermoset polymer molding, based on the flame-retardant thermoplastic or thermoset polymer molding composition or the flame-retardant thermoplastic or thermoset polymer molding.

Suitable further flame retardants are, for example, aryl phosphates, phosphonates, salts of hypophosphorous acid and red phosphorus, brominated aromatic or cycloaliphatic hydrocarbons, phenols or ethers, chloroparaffin, hexachlorocyclopentadiene adducts.

in addition, it is possible to add at least one synergist or phosphorus-nitrogen flame retardant to the flame-retardant thermoplastic or thermoset polymer molding composition or to the flame-retardant thermoplastic or thermoset polymer molding.

Preference is given to adding 0 to 40% by weight of synergist or phosphorus-nitrogen flame retardant to the flame-retardant thermoplastic or thermoset polymer molding composition or to the flame-retardant thermoplastic or thermoset polymer molding, based on the flame-retardant thermoplastic or thermoset polymer molding composition or the flame-retardant thermoplastic or thermoset polymer molding.

The synergists or phosphorus-nitrogen flame retardants are preferably condensation products of melamine and/or reaction products of melamine with phosphoric acid, and/or reaction products of condensation products of melamine with polyphosphoric acid and/or antimony oxide or mixtures thereof.

The synergist or phosphorus-nitrogen flame retardant is preferably melam, melem, melon, dimelamine pyrophosphate, melamine polyphosphate, melam polyphosphate, melon polyphosphate and melem polyphosphate, or mixed poly salts thereof.

The phosphorus-nitrogen flame retardants are preferably also nitrogen-containing phosphates of the formulae $(NH_4)_y H_{3-y} PO_4$ and $(NH_4 PO_3)_z$, where y is 1 to 3 and z is 1 to 10 000.

These are preferably ammonium hydrogenphosphate, ammonium dihydrogenphosphate and/or ammonium polyphosphate.

The nitrogen-containing synergists are preferably also benzoguanamine, tris(hydroxyethyl)isocyanurate, allantoin, glycoluril, melamine, melamine cyanurate, dicyandiamide and/or guanidine.

Also in accordance with the invention are synergistic combinations of the phosphinates mentioned with nitrogen-containing compounds (DE-A-196 14 424, DE-A-197 34 437 and DE-A-197 37 727).

Suitable synergists also include carbodiimides, zinc borate, condensation products of melamine (WO-A-96/16948), reaction products of melamine with phosphoric acid or condensed phosphoric acids, or reaction products of condensation products of melamine with phosphoric acid or condensed phosphoric acids, and mixtures of the products mentioned (WO-A-98/39306).

In addition, it is possible to add at least one stabilizer to the flame-retardant thermoplastic or thermoset polymer molding composition or to the flame-retardant thermoplastic or thermoset polymer molding, for example zinc salts, basic or amphoteric oxides, hydroxides, carbonates, silicates, borates, stannates, mixed oxide-hydroxides, oxide-hydroxide-carbonates, hydroxide-silicates or hydroxide-borates, phosphonite, phosphite or a phosphonite/phosphite mixture, or an ester or a salt of long-chain aliphatic carboxylic acids (fatty acids), which typically have chain lengths of $C_{14}$ to $C_{40}$.

Preference is given to adding 0 to 15% by weight of stabilizer to the flame-retardant thermoplastic or thermoset polymer molding composition or to the flame-retardant thermoplastic or thermoset polymer molding, based on the flame-retardant thermoplastic or thermoset polymer molding composition or the flame-retardant thermoplastic or thermoset polymer molding.

This stabilizer is preferably magnesium oxide, calcium oxide, aluminum oxide, zinc oxide, manganese oxide, tin oxide, aluminum hydroxide, boehmite, dihydrotalcite, hydrocalumite, magnesium hydroxide, calcium hydroxide, zinc hydroxide, tin oxide hydrate, manganese hydroxide, zinc borate, basic zinc silicate and/or zinc stannate.

The stabilizers preferably comprise alkali metal, alkaline earth metal, aluminum and/or zinc salts of long-chain fatty acids having 14 to 40 carbon atoms and/or reaction products of long-chain fatty acids having 14 to 40 carbon atoms with polyhydric alcohols such as ethylene glycol, glycerol, trimethylolpropane and/or pentaerythritol.

These stabilizers preferably comprise esters or salts of stearic acid, for example glyceryl monostearate or calcium stearate, or reaction products of montan wax acids with ethylene glycol, for example a mixture of ethylene glycol mono-montan wax ester, ethylene glycol di-montan wax ester, montan wax acids and ethylene glycol, or reaction products of montan wax acids with a calcium salt.

These reaction products are preferably a mixture of 1,3-butanediol mono-montan wax ester, 1,3-butanediol di-montan wax ester, montan wax acids, 1,3-butanediol, calcium montanate and the calcium salt.

It is possible to add further additives to the flame-retardant thermoplastic or thermoset polymer molding composition or to the flame-retardant thermoplastic or thermoset polymer molding, for example antioxidants, UV absorbers and light stabilizers, metal deactivators, peroxide-destroying compounds, polyamide stabilizers, basic co-stabilizers, nucleating agents and other additives.

Preference is given to adding 0 to 15% by weight of further additives to the flame-retardant thermoplastic or thermoset polymer molding composition or to the flame-retardant thermoplastic or thermoset polymer molding, based on the flame-retardant thermoplastic or thermoset polymer molding composition or the flame-retardant thermoplastic or thermoset polymer molding.

Suitable antioxidants are, for example, alkylated monophenols, e.g. 2,6-di-tert-butyl-4-methylphenol; 1,2-alkylthiomethylphenols, e.g. 2,4-dioctylthiomethyl-6-tert-butylphenol; hydroquinones and alkylated hydroquinones, e.g. 2,6-di-tert-butyl-4-methoxyphenol; tocopherols, e.g. α-tocopherol, β-tocopherol, γ-tocopherol, δ-tocopherol and mixtures thereof (vitamin E); hydroxylated thiodiphenyl ethers, e.g. 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-di-methyl-4-hydroxyphenyl)disulfide; alkylidenebisphenols, e.g. 2,2'-methylenebis(6-tert-butyl-4-methylphenol); O-, N- and S-benzyl compounds, e.g. 3,5,3',5'-tetra-tert-butyl-4,4'-dihydroxydibenzyl ether; hydroxybenzylated malonates, e.g. dioctadecyl 2,2-bis(3,5-di-tert-butyl-2-hydroxybenzyl)malonate; hydroxybenzyl aromatics, e.g. 1,3,5-tris-(3,5-di-tert-butyl)-4-hydroxybenzyl)-2,4,6-trimethylbenzene, 1,4-bis(3, 5-di-tert-butyl-4-hydroxybenzyl)-2,3,5,6-tetramethylbenzene, 2,4,6-tris-(3,5-di-tert-butyl-4-hydroxybenzyl)phenol; triazine compounds, e.g. 2,4-bisoctylmercapto-6-(3,5-di-tert-butyl-4-hydroxyanilino)-1, 3,5-triazine; benzyl phosphonates, e.g. dimethyl 2,5-di-tert-butyl-4-hydroxybenzylphosphonate; acylaminophenols, 4-hydroxylauramide, 4-hydroxystearanilide, N-(3,5-di-tert-butyl-4-hydroxyphenyl)carbamic acid octyl ester; esters of β-(3,5-di-tert-butyl-4-hydroxyphenyl)propionic acid with mono- or polyhydric alcohols; esters of β-(5-tert-butyl-4-hydroxy-3-methylphenyl)propionic acid with mono- or polyhydric alcohols; esters of β-(3,5-dicyclohexyl-4-hydroxyphenyl)propionic acid with mono- or polyhydric alcohols; esters of 3,5-di-tert-butyl-4-hydroxyphenylacetic acid with mono- or polyhydric alcohols; amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3, 5-di-tert-butyl-4-hydroxyphenylpropionyl)hydrazine.

Suitable UV absorbers and light stabilizers are, for example, 2-(2'-hydroxyphenyl)benzotriazoles, for example 2-(2'-hydroxy-5'-methylphenyl)benzotriazole;
2-hydroxybenzophenones, for example the 4-hydroxy, 4-methoxy, 4-octoxy, 4-decyloxy, 4-dodecyloxy, 4-benzyloxy, 4,2',4-trihydroxy, 2'-hydroxy-4,4'-dimethoxy derivative;
esters of optionally substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate; acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamante, N-(β-carbomethoxy-β-cyanovinyl)-2-methylindoline.

In addition, nickel compounds, for example nickel complexes of 2,2'-thiobis-[4(1,1,3,3-tetramethylbutyl)phenol], such as the 1:1 or the 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as those of the methyl or ethyl ester, nickel complexes of ketoximes, such as those of 2-Hydroxy-4-methylphenyl undecyl ketoxime, nickel complexes of 1-phenyl-4-lauroyl-5-hydroxy-pyrazole, optionally with additional ligands; sterically hindered amines, for example bis(2,2,6,6-tetramethylpiperidyl)sebacate; oxalamides, for example 4, 4'-dioctyloxyoxanilide; 2-(2-hydroxyphenyl)-1, 3,5-triazines, for example 2, 4,6-tris(2-hydroxy-4-octyloxyphenyl)-1,3,5-triazine.

Suitable metal deactivators are, for example, N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide, oxanilide, isophthalic dihydrazide, sebacic bisphenylhydrazide; N,N'-diacetyladipic dihydrazide, N,N'-bis(salicyloyl)oxalic dihydrazide, N,N'-bis(salicyloyl)thiopropionic dihydrazide.

Suitable peroxide-destroying compounds are, for example, esters of β-thiodipropionic acid (lauryl, stearyl, myristyl or tridecyl esters), mercaptobenzimidazole, the zinc salt of 2-mercaptobenzimidazole, zinc dibutyldithiocarbamate, dioctadecyl disulfide, pentaerythrityl tetrakis(β-dodecylmercapto)propionate.

Suitable basic co-stabilizers are melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium behenate, magnesium stearate, sodium ricinoleate, potassium palmitate, antimony catecholate or tin catecholate.

Suitable nucleating agents are, for example, 4-tert-butylbenzoic acid, adipic acid and diphenylacetic acid.

The other additives include, for example, plasticizers, expandable graphite, lubricants, emulsifiers, pigments, optical brighteners, antistats, blowing agents, heat stabilizers, impact modifiers, processing aids, antidripping agents, compatibilizers, nucleating agents, additives for laser marking, hydrolysis stabilizers, chain extenders and/or plasticizing agents.

It is possible to add further fillers and reinforcers to the flame-retardant thermoplastic or thermoset polymer molding composition or to the flame-retardant thermoplastic or thermoset polymer molding. Examples of fillers and reinforcers include calcium carbonate, silicates, glass fibers, asbestos, talc, kaolin, mica, barium sulfate, metal oxides and hydroxides, carbon black, graphite and others.

Preference is given to adding 0 to 70% by weight of filler and/or reinforcers to the flame-retardant thermoplastic or thermoset polymer molding composition or to the flame-retardant thermoplastic or thermoset polymer molding, based on the flame-retardant thermoplastic or thermoset polymer molding composition or the flame-retardant thermoplastic or thermoset polymer molding.

The metal oxides are preferably magnesium oxide, calcium oxide, aluminum oxide, zinc oxide, manganese oxide and/or tin oxide.

The hydroxides are preferably aluminum hydroxide, boehmite, magnesium hydroxide, hydrotalcite, hydrocalumite, calcium hydroxide, zinc hydroxide, tin oxide hydrate and/or manganese hydroxide.

The flame-retardant thermoplastic or thermoset polymer molding compositions and moldings preferably comprise
50 to 98% by weight of polymer,
2 to 50% by weight of mixture of alkylphosphonous salt (V) and dialkylphosphinic salt (VI),
0 to 50% by weight of further flame retardants,
0 to 40% by weight of synergists,
0 to 15% by weight of stabilizers,
0 to 15% by weight of further additives,
0 to 60% by weight of fillers.

The flame-retardant thermoplastic or thermoset polymer molding compositions and moldings preferably comprise
70 to 97% by weight of polymer,
3 to 30% by weight of mixture of alkylphosphonous salt (V) and dialkylphosphinic salt (VI),
0 to 30% by weight of further flame retardants,
0 to 10% by weight of synergists,
0 to 5% by weight of stabilizers,
0 to 5% by weight of further additives,
0 to 60% by weight of fillers.

The flame-retardant thermoplastic or thermoset polymer molding compositions and moldings preferably comprise
20 to 67% by weight of polymer,
3 to 20% by weight of mixture of alkylphosphonous salt (V) and dialkylphosphinic salt (VI),
0 to 30% by weight of further flame retardants,
0 to 10% by weight of synergists,
0 to 3% by weight of stabilizers,
0 to 3% by weight of further additives,
30 to 60% by weight of fillers.

The flame-retardant thermoplastic or thermoset polymer molding compositions and moldings preferably comprise
10 to 67% by weight of polymer,
5 to 10.5% by weight of mixture of alkylphosphonous salt (V) and dialkylphosphinic salt (VI),
0.1 to 10% by weight of further flame retardants,
0.1 to 8% by weight of synergists,
0.1 to 1% by weight of stabilizers,
0.1 to 1.5% by weight of further additives,
30 to 60% by weight of fillers.

The flame-retardant thermoplastic or thermoset polymer molding compositions and moldings preferably comprise
40 to 96.9% by weight of polymer,
3 to 30% by weight of mixture of alkylphosphonous salt (V) and dialkylphosphinic salt (VI),
0 to 30% by weight of further flame retardants,
0 to 10% by weight of synergists,
0 to 3% by weight of stabilizers,
0 to 3% by weight of further additives,
0.1 to 30% by weight of fillers.

The flame-retardant thermoplastic or thermoset polymer molding compositions and moldings preferably comprise
25 to 67% by weight of polymer,
5 to 17.5% by weight of mixture of alkylphosphonous salt (V) and dialkylphosphinic salt (VI),
0.1 to 15% by weight of further flame retardants,
0.1 to 10% by weight of synergists,
0.1 to 1% by weight of stabilizers,
0.1 to 1.5% by weight of further additives,
0.1 to 30% by weight of fillers.

These additional flame retardants, synergists, phosphorus-nitrogen flame retardants, stabilizers, further additives and fillers can be added to the polymers before, together with or after addition of the mixture of alkylphosphonous salt (V) and dialkylphosphinic salt (VI). The metered addition can be effected in solid form, in a solution or melt, or else in the form of solid or liquid mixtures or as masterbatches/concentrates.

The aforementioned further flame retardants, synergists, phosphorus-nitrogen flame retardants, stabilizers, further additives, fillers and the mixture of alkylphosphonous salt (V) and dialkylphosphinic salt (VI) can be introduced into the polymer in a wide variety of different process steps. For instance, it is possible in the case of polyamides or polyesters, at the start or at the end of the polymerization/polycondensation or in a subsequent compounding operation, to mix the further flame retardants, synergists, phosphorus-nitrogen flame retardant, stabilizers, further additives, fillers and the mixture of alkylphosphonous salt (V) and dialkylphosphinic salt (VI) into the polymer melt. In addition, there are processing operations in which the further flame retardants, synergists, phosphorus-nitrogen flame retardants, stabilizers, further additives, fillers and the mixture of alkylphosphonous salt (V) and dialkylphosphinic salt (VI) are not added until a later stage. This is practiced especially in the case of use of pigment or additive masterbatches. There is also the possibility of applying further flame retardants, synergists, phosphorus-nitrogen flame retardants, stabilizers, further additives, fillers and the mixture of alkylphosphonous salt (V) and dialkylphosphinic salt (VI), particularly in pulverulent form, to the polymer pellets, which may be warm as a result of the drying operation, by drum application.

The mixture of alkylphosphonous salt (V) and dialkylphosphinic salt (VI) is preferably in the form of pellets, flakes, fine grains, powder and/or micronizate.

The mixture of alkylphosphonous salt (V) and dialkylphosphinic salt (VI) is preferably also in the form of a physical mixture of the solids, of a melt mixture, of a compactate, of an extrudate, or in the form of a masterbatch.

Suitable polyesters derive from dicarboxylic acids and esters thereof and diols and/or from hydroxycarboxylic acids or the corresponding lactones. Particular preference is given to using terephthalic acid and ethylene glycol, propane-1,3-diol and butane-1,3-diol.

Suitable polyesters include polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and block polyether esters which derive from polyethers with hydroxyl end groups; and also polyesters modified with polycarbonates or MBS.

The flame-retardant polyester molding compositions produced in accordance with the invention are preferably used in polyester moldings.

Preferred polyester moldings are filaments, fibers, films and moldings, which comprise mainly terephthalic acid as the dicarboxylic acid components and mainly ethylene glycol as the diol component.

Preferably, the resulting phosphorus content in filaments and fibers produced from flame-retardant polyester is 0.1-18%, preferably 0.5-15%, and, in the case of films, 0.2-15%, preferably 0.9-12% by weight.

Suitable polystyrenes are polystyrene, poly(p-methylstyrene) and/or poly(alpha-methylstyrene).

The suitable polystyrenes are preferably copolymers of styrene or alpha-methylstyrene with dienes or acrylic derivatives, for example styrene-butadiene, styrene-acrylonitrile, styrene-alkyl methacrylate, styrene-butadiene-alkyl acrylate and methacrylate, styrene-maleic anhydride, styrene-acrylonitrile-methyl acrylate; more impact-resistant mixtures of styrene copolymers and another polymer, for example a poly-acrylate, a diene polymer or an ethylene-propylene-diene terpolymer; and block copolymers of styrene, for example styrene-butadiene-styrene, styrene-isoprene-styrene, styrene-ethylene/butylene-styrene or styrene-ethylene/propylene-styrene.

The suitable polystyrenes are preferably also graft copolymers of styrene or alpha-methylstyrene, for example styrene onto polybutadiene, styrene onto polybutadiene-styrene or polybutadiene-acrylonitrile copolymers, styrene and acrylonitrile (or methacrylonitrile) onto polybutadiene; styrene, acrylonitrile and methyl methacrylate onto polybutadiene; styrene and maleic anhydride onto polybutadiene; styrene, acrylonitrile and maleic anhydride or maleimide onto polybutadiene; styrene and maleimide onto polybutadiene, styrene and alkyl acrylates or alkyl methacrylates onto polybutadiene, styrene and acrylonitrile onto ethylene-propylene-diene terpolymers, styrene and acrylonitrile onto polyalkyl acrylates or polyalkyl methacrylates, styrene and acrylonitrile onto acrylate-butadiene copolymers, and mixtures thereof, as known, for example, as what are called ABS, MBS, ASA or AES polymers.

The polymers are preferably polyamides and copolyamides which derive from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7,7, nylon-8,8, nylon-9,9, nylon-10,9, nylon-10,10, nylon-11, nylon-12, etc. These are known, for example, by the trade names Nylon®, from DuPont, Ultramid®, from BASF, Akulon® K122, from DSM, Zytel® 7301, from DuPont; Durethan® B 29, from Bayer and Grillamid®, from Ems Chemie.

Also suitable are aromatic polyamides proceeding from m-xylene, diamine and adipic acid; polyamides prepared from hexamethylenediamine and iso- and/or terephthalic acid and optionally an elastomer as a modifier, for example poly-2,4,4-trimethylhexamethyleneterephthalamide or poly-m-phenyleneisophthalamide, block copolymers of the aforementioned polyamides with polyolefins, olefin copolymers, ionomers or chemically bound or grafted elastomers, or with polyethers, for example with polyethylene glycol, polypropylene glycol or polytetramethylene glycol. In addition, EPDM- or ABS-modified polyamides or copolyamides; and polyamides condensed during processing ("RIM polyamide systems").

The invention finally also relates to a process for producing flame-retardant polymer moldings, wherein inventive flame-retardant polymer molding compositions are processed by injection molding (for example injection molding machine of the Aarburg Alirounder type) and pressing, foam injection molding, internal gas pressure injection molding, blow molding, film casting, calendering, laminating or coating at elevated temperatures to give the flame-retardant polymer molding.

Preferably, the thermoset polymers comprise unsaturated polyester resins (UP resins) which derive from copolyesters of saturated and unsaturated dicarboxylic acids or anhydrides thereof with polyhydric alcohols, and vinyl compounds as crosslinking agents. UP resins are cured by free-radical polymerization with initiators (e.g. peroxides) and accelerators.

Preferred unsaturated dicarboxylic acids and derivatives for preparation of the polyester resins are maleic anhydride and fumaric acid.

Preferred saturated dicarboxylic acids are phthalic acid, isophthalic acid, terephthalic acid, tetrahydrophthalic acid, adipic acid.

Preferred diols are 1,2-propanediol, ethylene glycol, diethylene glycol and neopentyl glycol, neopentyl glycol, ethoxylated or propoxylated bisphenol A.

A preferred vinyl compound for crosslinking is styrene.

Preferred curative systems are peroxides and metal coinitiators, for example hydroperoxides and cobalt octanoate and/or benzoyl peroxide and aromatic amines and/or UV light and photosensitizers, e.g. benzoin ethers.

Preferred hydroperoxides are di-tert-butyl peroxide, tert-butyl peroctoate, tert-butyl perpivalate, tert-butyl per-2-ethylhexanoate, tert-butyl permaleate, tert-butyl perisobutyrate, benzoyl peroxide, diacetyl peroxide, succinyl peroxide, p-chlorobenzoyl peroxide, dicyclohexyl peroxodicarbonate.

Preferably, initiators are used in amounts of 0.1 to 20% by weight, preferably 0.2 to 15% by weight, based on the mass of all comonomers.

Preferred metal coinitiators are compounds of cobalt, manganese, iron, vanadium, nickel or lead. Preferably, metal coinitiators are used in amounts of 0.05 to 1% by weight, based on the mass of all comonomers.

Preferred aromatic amines are dimethylaniline, dimethyl-p-toluene, diethylaniline and phenyldiethanolamine.

In one process for preparing flame-retardant copolymers, at least one ethylenically unsaturated dicarboxylic anhydride derived from at least one $C_4$-$C_8$-dicarboxylic acid, at least one vinylaromatic compound and a polyol are copolymerized, and reacted with inventive adducts of alkylphosphonous acid derivatives and diester-forming olefins.

In one process for producing flame-retardant thermoset compositions, a thermoset resin is mixed with inventive mixture of alkylphosphonous salt (V) and dialkylphosphinic salt (VI) and further flame retardants, synergists, stabilizers, further additives and fillers or reinforcers, and the resulting mixture is wet pressed at pressures of 3 to 10 bar and temperatures of 20 to 60° C. (cold pressing).

In a further process for producing flame-retardant thermoset compositions, a thermoset resin is mixed with inventive mixture of alkylphosphonous salt (V) and dialkylphosphinic salt (VI) and further flame retardants, synergists, stabilizers, further additives and fillers or reinforcers, and the resulting mixture is wet pressed at pressures of 3 to 10 bar and temperatures of 80 to 150° C. (warm or hot pressing).

Preferably, the polymers are crosslinked epoxy resins which derive from aliphatic, cycloaliphatic, heterocyclic or aromatic glycidyl compounds, for example from bisphenol A diglycidyl ethers, bisphenol F diglycidyl ethers, which are crosslinked by means of customary hardeners and/or accelerators.

Suitable glycidyl compounds are bisphenol A diglycidyl esters, bisphenol F diglycidyl esters, polyglycidyl esters of phenol formaldehyde resins and cresol-formaldehyde resins, polyglycidyl esters of phthalic acid, isophthalic acid and terephthalic acid, and of trimellitic acid, N-glycidyl compounds of aromatic amines and heterocyclic nitrogen bases, and di- and polyglycidyl compounds of polyhydric aliphatic alcohols.

Suitable hardeners are aliphatic, cycloaliphatic, aromatic and heterocyclic amines or polyamines, such as ethylenediamine, diethylenetriamine triethylenetetramine, propane-1,3-diamine, hexamethylenediamine, aminoethylpiperazine, isophoronediamine, polyamidoamine, diaminodiphenylmethane, diaminodiphenyl ether, diaminodiphenyl sulfone, aniline-formaldehyde resins, 2,2,4-trimethylhexane-1,6-diamine, m-xylylenediamine, bis(4-aminocyclohexyl)methane, 2,2-bis(4-aminocyclohexyl)propane, 3 aminomethyl-3,5,5-trimethylcyclohexylamine (isophoronediamine), polyamidoamines, cyanoguanidine and dicyandiamide, and likewise polybasic acids or anhydrides thereof, for example phthalic anhydride, maleic anhydride, tetrahydrophthalic anhydride, methyltetrahydrophthalic anhydride, hexahydrophthalic anhydride and methylhexahydrophthalic anhydride, and also phenols, for example phenol-novolac resin, cresol-novolac resin, dicyclopentadiene-phenol adduct resin, phenol aralkyl resin, cresolaralkyl resin, naphtholaralkyl resin, biphenol-modified phenolaralkyl resin, phenol-trimethylolmethane resin, tetraphenylolethane resin, naphthol-novolac resin, naphthol-phenol cocondensate resin, naphthol-cresol cocondensate resin, biphenol-modified phenol resin and aminotriazine-modified phenol resin. All hardeners can be used alone or in combination with one another.

Suitable catalysts or accelerators for the crosslinking in the polymerization are tertiary amines, benzyldimethylamine, N-alkylpyridines, imidazole, 1-methylimidazole, 2 methylimidazole, 2-ethyl-4-methylimidazole, 2-ethyl-4-methylimidazole, 2 phenylimidazole, 2-heptadecylimidazole, metal salts of organic acids, Lewis acids and amine complex salts.

The formulation of the invention may also comprise other additives which are commonly used in epoxy resin formulations, such as pigments, dyes and stabilizers.

Epoxy resins are suitable for potting of electrical or electronic components and for saturation and impregnation processes. In electrical engineering, epoxy resins are predominantly rendered flame-retardant and used for printed circuit boards and insulators.

Preferably, the polymers are crosslinked polymers which derive from aldehydes on the one hand, and phenols, urea or melamine on the other hand, such as phenol-formaldehyde, urea-formaldehyde and melamine-formaldehyde resins. The polymers preferably comprise crosslinkable acrylic resins which derive from substituted acrylic esters, for example from epoxy acrylates, urethane acrylates or polyester acrylates.

Preferably, the polymers are alkyd resins, polyester resins and acrylate resins which have been crosslinked with melamine resins, urea resins, isocyanates, isocyanurates, polyisocyanates or epoxy resins.

Preferred polyols are alkene oxide adducts of ethylene glycol, 1,2-propanediol, bisphenol A, trimethylolpropane, glycerol, pentaerythritol, sorbitol, sugars, degraded starch, ethylenediamine, diaminotoluene and/or aniline, which serve as initiators. The preferred alkoxylating agents preferably contain 2 to 4 carbon atoms, particular preference being given to ethylene oxide and propylene oxide.

Preferred polyester polyols are obtained by polycondensation of a polyalcohol such as ethylene glycol, diethylene glycol, propylene glycol, 1,4-butanediol, 1,5-pentanediol, methylpentanediol, 1,6-hexanediol, trimethylolpropane, glycerol, pentaerythritol, diglycerol, glucose and/or sorbitol, with a dibasic acid such as oxalic acid, malonic acid, succinic acid, tartaric acid, adipic acid, sebacic acid, maleic acid, fumaric acid, phthalic acid and/or terephthalic acid. These polyester polyols can be used alone or in combination.

Suitable polyisocyanates are aromatic, alicyclic or aliphatic polyisocyanates having not fewer than two isocyanate groups and mixtures thereof. Preference is given to aromatic polyisocyanates such as tolyl diisocyanate, methylene diphenyl diisocyanate, naphthylene diisocyanate, xylylene diisocyanate, tris(4-isocyanatophenyl)methane and polymethylenepolyphenylene diisocyanates; alicyclic polyisocyanates such as methylenediphenyl diisocyanate, tolyl diisocyanate; aliphatic polyisocyanates and hexamethylene diisocyanate, isophorone diisocyanate, dimeryl diisocyanate, 1,1-methylenebis(4-isocyanatocyclohexane-4,4'-diisocyanatodicyclohexylmethane isomer mixture, 1,4-cyclohexyl diisocyanate, Desmodur® products (Bayer) and lysine diisocyanate and mixtures thereof.

Suitable polyisocyanates are modified products which are obtained by reaction of polyisocyanate with polyol, urea, carbodiimide and/or biuret.

Suitable catalysts for preparation of polyurethane are strong bases, alkali metal salts of carboxylic acids or aliphatic tertiary amines. Preference is given to quaternary ammonium hydroxide, alkali metal hydroxide or alkoxide, sodium acetate or potassium acetate, potassium octoate, sodium benzoate, 1,4-diazabicyclo[2.2.2]octane, N,N,N',N'-tetramethylhexamethylenediamine, N,N,N',N'-tetramethylpropylenediamine, N,N,N',N',N''-pentamethyldiethylenetriamine, N,N'-di($C_1$-$C_2$)-alkylpiperazine, trimethylaminoethylpiperazine, N,N-dimethylcyclohexylamine, N,N-dimethylbenzylamine, N-methylmorpholine, N-ethylmorpholine, trimethylamine, triethylamine, tributylamine, triethylenediamine, bis(dimethylaminoalkyl)piperazines, N,N,N',N'-tetramethylethylenediamine, N,N-diethylbenzylamine, bis(N,N-diethylaminoethyl)adipate, N,N,N',N'-tetramethyl-1,3-butanediamine, N,N-diethyl-[beta]-phenylethylamine, 1,2-dimethylimidazole, 2-methylimidazole etc.

Preferably, the weight ratio of the polyisocyanate to polyol is 170 to 70 parts by weight, preferably 130 to 80 parts by weight, based on 100 parts by weight of the polyol.

Preferably, the weight ratio of the catalyst is 0.1 to 4 parts by weight, preferably 1 to 2 parts by weight, based on 100 parts by weight of the polyol.

Preferred blowing agents for polyurethanes are water, hydrocarbons, hydrochlorofluorocarbon, hydrofluorocarbon etc. The amount of the blowing agent for polyurethanes is 0.1 to 1.8 parts by weight, preferably 0.3 to 1.6 parts by weight and especially 0.8 to 1.6 parts by weight, based on 100 parts by weight of the polyol.

The invention is illustrated by the examples which follow.
Chemicals and Abbreviations Used Deloxan® THP II metal scavenger (from Evonik Industries AG)

EXAMPLE 1

1500 g (14 mol) of sodium hypophosphite monohydrate and 35 g of concentrated sulfuric acid are dissolved in 7.5 kg of water and initially charged in a 16 l steel-enamel jacketed pressure reactor. After heating the reaction mixture to 100° C., a reducing valve set to 6 bar is used to introduce ethylene into the reactor up to saturation. While stirring constantly at an ethylene pressure of 3 bar and a temperature of about 100° C., a solution of 80 g (5 mol %) of hydrogen peroxide (33% by weight) in 300 g of water is metered in homogeneously. At a conversion of ethylene of 90%, the metered addition of hydrogen peroxide is stopped and the reactor is decompressed. After cooling to about 90° C., 746 g (4.67 mol of aluminum) of aluminum acetate in 2254 g of water are added within 60 minutes. Subsequently, the resulting solid is filtered off, washed with 2 l of hot water and dried at 130° C. under reduced pressure. The resulting mixture comprises diethylphosphinic acid aluminum(III) salt and ethylphosphonous acid aluminum(III) salt in a ratio of 88.6% by weight of diethylphosphinic acid aluminum(III) salt and 11.4% by weight of ethylphosphonous acid aluminum(III) salt (92.6% yield).

EXAMPLE 2

A solution of 636 g (6 mol) of sodium hypophosphite monohydrate in 3 kg of water is initially charged in a 10 l jacketed pressure reactor. After heating the reaction solution to 100° C., a reducing valve set to 6 bar is used to introduce ethylene into the reactor up to saturation. At an ethylene pressure of 6 bar and a temperature of 100-110° C., while stirring constantly, a 0.4 molar sodium peroxodisulfate solution is metered into the reaction solution homogeneously at a metering rate of 25 ml/h. Once a particular conversion of ethylene has been attained, the metered addition of sodium peroxodisulfate solution is stopped and the reactor is decompressed. At 85° C., a mixture of 1291 g of a 46% aqueous solution of $Al_2(SO_4)_3 \cdot 14H_2O$ is added. Subsequently, the resulting solid is filtered off, washed with hot water and dried at 130° C. under reduced pressure. Table 4 lists the conversion of ethylene (Reaction conversion), the ratio of diethylphosphinic acid aluminum(III) salt and ethylphosphonous acid aluminum(III)salt (diethylphosphinic acid Al salt/ethylphosphonous acid Al salt) and the yield of mixture obtained.

TABLE 1

| Reaction conversion [%] | Diethylphosphinic acid Al salt/ ethylphosphonous acid Al salt [%] | Yield [%] |
| --- | --- | --- |
| 82.2 | 75/25 | 94.6 |
| 85.3 | 80/20 | 95.8 |
| 91.5 | 90/10 | 97.5 |
| 95.7 | 95/5 | 98.3 |

EXAMPLE 3

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 20 bar is used to introduce ethylene into the reactor up to saturation. While stirring constantly at an ethylene pressure of 20 bar and a temperature of 100-110° C., a solution of 32 g (1 mol %) of ammonium peroxodisulfate in 300 g of water is metered in homogeneously. At a conversion of ethylene of 90%, the metered addition of ammonium peroxodisulfate is stopped and the reactor is decompressed. After cooling to about 90° C., 3000 g (4.67 mol of aluminum) of a 46% aqueous solution of $Al_2(SO_4)_3 \cdot 14H_2O$ is added within 60 minutes. Subsequently, the resulting solid is filtered off and dried at 130° C. under reduced pressure. The resulting mixture comprises diethylphosphinic acid aluminum(III) salt and ethylphosphonous acid aluminum(III) salt in a ratio of 87.3% by weight of diethylphosphinic acid aluminum (III) salt and 12.7% by weight of ethylphosphonous acid aluminum(III) salt (96.3% yield).

EXAMPLE 4

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar is used to introduce ethylene into the reactor up to saturation. While stirring constantly at an ethylene pressure of 6 bar and a temperature of 100-110° C., a solution of 19 g (0.5 mol %) of 2,2'-azobis(2-amidinopropane) hydrochloride in 300 g of water is metered in homogeneously. At a conversion of ethylene of 87.3%, the metered addition of 2,2'-azobis(2-amidinopropane) hydrochloride is stopped and the reactor is decompressed. After cooling to about 90° C., 650 g (4.67 mol of aluminum) of aluminum chloride hexahydrate in 2350 g of water were added within 60 minutes. Subsequently, the resulting solid is filtered off, washed with 2 l of hot water and dried at 130° C. under reduced pressure. The resulting mixture comprises diethylphosphinic acid aluminum(III) salt and ethylphosphonous acid aluminum(III) salt in a ratio of 83.3% by weight of diethylphosphinic acid aluminum(III) salt and 16.7% by weight of ethylphosphonous acid aluminum(III) salt (95.9% yield).

EXAMPLE 5

1500 g (14 mol) of sodium hypophosphite monohydrate and 14 g of concentrated sulfuric acid are dissolved in 7.5 kg of water and initially charged in a 16 l steel-enamel jacketed pressure reactor. After heating the reaction mixture to 100° C., a reducing valve set to 6 bar is used to introduce ethylene into the reactor up to saturation. While stirring constantly at an ethylene pressure of 6 bar and a temperature of 100-110° C., a solution of 22 g (1 mol %) of sodium percarbonate in 300 g of water is metered in homogeneously. At a conversion of ethylene of 83.5%, the metered addition of sodium percarbonate is stopped and the reactor is decompressed. After cooling to about 90° C., 3000 g (4.67 mol of aluminum) of a 46% aqueous solution of $Al_2(SO_4)_3 \cdot 14H_2O$ were added within 60 minutes. Subsequently, the resulting solid is filtered off, washed with 2 l of hot water and dried at 130° C. under reduced pressure. The resulting mixture comprises diethylphosphinic acid aluminum(III) salt and ethylphosphonous acid aluminum(III) salt in a ratio of 76.4% by weight of diethylphosphinic acid aluminum(III) salt and 23.6% by weight of ethylphosphonous acid aluminum(III) salt (95.0% yield).

EXAMPLE 6

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar is used to introduce ethylene into the reactor up to saturation. While stirring constantly at an ethylene pressure of 6 bar and a temperature of 100-110° C., a solution of 22 g (1 mol %) of sodium percarbonate and 16 g of tetraacetylethylenediamine in 300 g of water is metered in homogeneously. At a conversion of ethylene of 85%, the metered addition of sodium percarbonate and tetraacetylethylenediamine is stopped and the reactor is decompressed. After cooling to about 90° C., 3000 g (4.67 mol of aluminum) of a 46% aqueous solution of $Al_2(SO_4)_3 \cdot 14H_2O$ is added within 60 minutes. Subsequently, the resulting solid was filtered off, washed with 2 l of hot water and dried at 130° C. under reduced pressure. The resulting mixture comprises diethylphosphinic acid aluminum(III) salt and ethylphosphonous acid aluminum(III) salt in a ratio of 79.5% by weight of diethylphosphinic acid aluminum(III) salt and 20.5% by weight of ethylphosphonous acid aluminum(III) salt (95.9% yield).

EXAMPLE 7

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar is used to introduce ethylene into the reactor up to saturation. While stirring constantly at an ethylene pressure of 6 bar and a temperature of 120-130° C., a solution of 49 g (1 mol %) of dibenzoyl peroxide (70% by weight in water) in 300 g of water is metered in homogeneously. At a conversion of ethylene of 93.8%, the metered addition of dibenzoyl peroxide is stopped and the reactor is decompressed. After cooling to about 90° C., 1725 g (4.67 mol of aluminum) of aluminum nitrate nonahydrate dissolved in 1275 g of water are added within 60 minutes. Subsequently, the resulting solid was filtered off, washed with 2 l of hot water and dried at 130° C. under reduced pressure. The resulting mixture comprises diethylphosphinic acid aluminum(III) salt and ethylphosphonous acid aluminum(III) salt in a ratio of 93.0% by weight of diethylphosphinic acid aluminum(III) salt and 7.0% by weight of ethylphosphonous acid aluminum(III) salt (96.4% yield).

EXAMPLE 8

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar was used to introduce ethylene into the reactor up to saturation. While stirring constantly at an ethylene pressure of 6 bar and a temperature of 100-110° C., a solution of 33 g (1 mol %) of sodium peroxodisulfate in 300 g of water is metered in homogeneously. At a conversion of ethylene of 85.3%, the metered addition of sodium peroxodisulfate is stopped and the reactor is decompressed. After cooling to about 90° C., 700 g of concentrated sulfuric acid are metered in within 30 minutes. Subsequently, 364 g (4.67 mol) of aluminum hydroxide are added and the mixture is heated to 150° C. in a closed reactor for 8 h. After cooling to ambient temperature, the resulting solid is filtered off, washed with 2 l of hot water and dried at 130° C. under reduced pressure. The resulting mixture comprises diethylphosphinic acid aluminum(III) salt and ethylphosphonous acid aluminum(III) salt in a ratio of 79.6% by weight of diethylphosphinic acid aluminum(III) salt and 20.4% by weight of ethylphosphonous acid aluminum(III) salt (89.7% yield).

EXAMPLE 9

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar was used to introduce ethylene into the reactor up to saturation. While stirring constantly at an ethylene pressure of 6 bar and a temperature of 100-110° C., a solution of 33 g (1 mol %) of sodium peroxodisulfate in 300 g of water is metered in homogeneously. At a conversion of ethylene of 85.3%, the metered addition of sodium peroxodisulfate is stopped and the reactor is decompressed. After cooling to about 90° C., 700 g of concentrated sulfuric acid are metered in within 30 min, the mixture is concentrated, acetic acid is added and sodium sulfate formed is filtered off. After concentrating again, 1190 g (3.5 mol) of titanium tetrabutoxide and 25 l of toluene are added and the mixture is heated under reflux for 40 h. During this period, about 750 ml of the toluene are distilled off together with the butanol formed and replaced by fresh toluene every 8 h. The solution formed is subsequently freed of the solvent used. The resulting mixture comprises diethylphosphinic acid titanium(IV) salt and ethylphosphonous acid titanium(IV) salt in a ratio of 76.3% by weight of diethylphosphinic acid titanium(IV) salt and 23.7% by weight of ethylphosphonous acid titanium(IV) salt (99.0% yield).

EXAMPLE 10

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar was used to introduce ethylene into the reactor up to saturation. While stirring constantly at an ethylene pressure of 6 bar and a temperature of 100-110° C., a solution of 33 g (1 mol %) of sodium peroxodisulfate in 300 g of water is metered in homogeneously. At a conversion of ethylene of 85.3%, the metered addition of sodium peroxodisulfate is stopped and the reactor is decompressed. After cooling to about 70° C., a solution of 2013 g of $ZnSO_4*7H_2O$ (7 mol) in 2.5 kg of water is metered in within 60 minutes. After 30 minutes, the resulting solid is filtered off, washed with 10 l of hot water and dried at 130° C. under reduced pressure. The resulting mixture comprises diethylphosphinic acid zinc(II) salt and ethylphosphonous acid zinc(II) salt in a ratio of 81.3% by weight of diethylphosphinic acid zinc(II) salt and 18.7% by weight of ethylphosphonous acid zinc(II) salt (79.4% yield).

EXAMPLE 11

1500 g (14 mol) of sodium hypophosphite monohydrate are dissolved in 7.5 kg of water and initially charged in a 16 l steel-enamel jacketed pressure reactor. After heating the reaction mixture to 100° C., a reducing valve set to 6 bar was used to introduce ethylene into the reactor up to saturation. While stirring constantly at an ethylene pressure of 6 bar and a temperature of 100-110° C., a solution of 33 g (1 mol %) of sodium peroxodisulfate in 300 g of water is metered in homogeneously. At a conversion of ethylene of 85.3%, the metered addition of sodium peroxodisulfate is stopped and the reactor is decompressed. After cooling to about 90° C., 700 g of concentrated sulfuric acid are metered in within 30 min, the mixture is concentrated, 1.5 kg of acetic acid are added, sodium sulfate formed is filtered off and 570 g (7 mol) of zinc oxide are added. The clear solution formed is subsequently freed of the solvent used. The resulting mixture comprises diethylphosphinic acid zinc(II) salt and ethylphosphonous acid zinc(II) salt in a ratio of 75.9% by weight of diethylphosphinic acid zinc(II) salt and 24.1% by weight of ethylphosphonous acid zinc(II) salt (99.0% yield).

EXAMPLE 12

1. Components Used
Commercial Polymers (Pellets):
nylon-6,6 (N 6,6-GR): Ultramid® A27 (from BASF AG, Germany)
polybutylene terephthalate (PBT) Ultradur® B4500 (from BASF AG, Germany)
Glass Fibers:
Vetrotex® 983 EC 10 4.5 mm (from Saint-Gobain-Vetrotex, Germany)
Vetrotex® 952 EC 10 4.5 mm (from Saint-Gobain-Vetrotex, Germany)
Flame Retardant (Component A):
aluminum salt of diethylphosphinic acid, referred to here as DEPAL
Flame Retardant (Component B):
mixture of ethylphosphonous acid aluminum salt (EPAL) and dialkylphosphinic acid aluminum salt (DEPAL) in a ratio of 25.0 to 75.0% by weight, referred to hereinafter as EPAL/DEPAL Synergist (Component C):
melamine polyphosphate (referred to as MPP), Melapur® 200 (from Ciba SC, Switzerland)
melamine cyanurate (referred to as MC), Melapur® MC50 (from Ciba SC, Switzerland)
melem, Delacal® 420 (from Delamin Ltd, UK)
Component D:
zinc borate, Firebrake® ZB and Firebrake® 500, from Borax, USA
dihydrotalcite, DHT 4A, from Kyowa Chemicals, Japan
Phosphonites (Component E):
Sandostab® P-EPQ, from Clariant, Germany
Wax Components (Component F):
Licomont® CaV 102, Clariant, Germany (calcium salt of montan wax acid)
Licowax® E, from Clariant, Germany (ester of montan wax acid)
Production, Processing and Testing of Flame-Retardant Polymer Molding Compositions:

The flame retardant components were mixed with the phosphonite, the lubricants and stabilizers in the ratio specified in the table and incorporated via the side intake of a twin-screw extruder (Leistritz ZSE 27/44D) into N 6,6 at temperatures of 260 to 310° C., and into PBT at 250-275° C. The glass fibers were added via a second side intake. The homogenized polymer strand was drawn off, cooled in a water bath and then pelletized.

After sufficient drying, the molding compositions were processed to test specimens on an injection molding machine (Arburg 320 C Allrounder) at melt temperatures of 250 to 300° C., and tested and classified for flame retardancy using the UL 94 test (Underwriter Laboratories).

The flowability of the molding compositions was determined by finding the melt volume flow rate (MVR) at 275° C./2.16 kg. A sharp rise in the MVR value indicates polymer degradation.

All tests in the respective series, unless stated otherwise, were performed under identical conditions (temperature programs, screw geometry, injection molding parameters, etc.) for comparability.

Formulations C-1 to C-3 are comparative examples in which a flame retardant combination based on the aluminum salt of diethylphosphinic acid (DEPAL) and the nitrogen-containing synergist melamine polyphosphate (MPP) and the metal oxide or borate alone were used.

The results in which the flame retardant-stabilizer mixture according to the invention was used are listed in examples I-1 to I-4. All amounts are reported as % by weight and are based on the polymer molding composition including the flame retardant mixture and additives.

TABLE 1

N 6,6 GF 30 test results.

|  | C-1 | C-2 | C-3 | I-1 | I-2 | I-3 | I-4 |
|---|---|---|---|---|---|---|---|
| nylon-6,6 | 49.55 | 49.55 | 49.55 | 49.55 | 49.55 | 49.55 | 49.55 |
| 983 glass fibers | 30 | 30 | 30 | 30 | 30 | 30 | 30 |
| A: DEPAL | 13 | 12 | 12 |  |  |  |  |
| B: EPAL/DEPAL |  |  |  | 17 | 16 | 16 | 20 |
| C: MPP | 7 | 7 | 7 | 3 | 3 | 3 |  |
| D1: zinc borate |  | 1 |  |  | 1 |  |  |
| D2: DHT4A |  |  | 1 |  |  | 1 |  |
| E: CaV 102 | 0.25 | 0.25 | 0.25 | 0.25 | 0.25 | 0.25 | 0.25 |
| F: P-EPQ | 0.20 | 0.20 | 0.20 | 0.20 | 0.20 | 0.20 | 0.20 |
| UL 94 0.8 mm | V-0 | V-0 | V-1 | V-0 | V-0 | V-0 | V-0 |
| MVR 275° C./2.16 kg | 19 | 12 | 14 | 5 | 3 | 4 | 3 |
| Exudation* | severe | marked | marked | low | none | low | none |
| Color | gray | white | white | white | white | white | white |
| Impact resistance [kJ/m$^2$] | 61 | 61 | 55 | 62 | 63 | 66 | 61 |
| Notched impact resistance [kJ/m$^2$] | 15 | 16 | 12 | 9.7 | 15 | 11 | 15 |

*14 days, 100% humidity, 70° C.

It is clear from the examples that the inventive mixtures of DEPAL, EPAL and optionally MPP and borate or hydrotalcite and components E and F clearly improve the processability of the polymers and the properties of the injection moldings, without impairing flame retardancy.

The incorporation of the DEPAL and MPP flame retardants into N 6,6 does lead to UL 94 V-0, but also to gray discoloration of the molding compositions, exudation and high melt indices (C-1). The addition of zinc borate or hydrotalcite can prevent the gray discoloration, and exudation declines markedly (C-2, C-3).

If an inventive flame retardant combination of DEPAL, EPAL and optionally nitrogen synergist, borate or hydrotalcite lubricant and stabilizer (I1-I4) is now used, the result is not only flame retardancy but also no discoloration, no exudation, low melt indices and good mechanical properties. The low melt index (MVR) shows that there is no polymer degradation.

TABLE 2

PBT GF 25 test results.

|  | C-4 | C-5 | C-6 | I-5 | I-6 | I-7 | I-8 |
|---|---|---|---|---|---|---|---|
| PBT | 49.55 | 49.55 | 49.55 | 49.55 | 49.55 | 49.55 | 49.55 |
| 952 glass fibers | 25 | 25 | 25 | 25 | 25 | 25 | 25 |
| A: DEPAL | 13.3 | 12 | 12 |  |  |  |  |
| B: EPAL/DEPAL |  |  |  | 17 | 16 | 16 | 20 |
| C1: MC | 7 | 7 | 7 | 3 | 3 | 3 |  |
| C2: MPP |  | 1 |  |  | 1 |  |  |
| C3: melem |  |  | 1 |  |  | 1 |  |
| E: Licowax E | 0.25 | 0.25 | 0.25 | 0.25 | 0.25 | 0.25 | 0.25 |
| F: P-EPQ | 0.20 | 0.20 | 0.20 | 0.20 | 0.20 | 0.20 | 0.20 |
| UL 94 0.8 mm | V-1 | V-1 | V-1 | V-0 | V-0 | V-0 | V-0 |
| Solution viscosity SV* | 1185 | 1201 | 1179 | 1382 | 1364 | 1338 | 1399 |

TABLE 2-continued

PBT GF 25 test results.

|  | C-4 | C-5 | C-6 | I-5 | I-6 | I-7 | I-8 |
|---|---|---|---|---|---|---|---|
| Elongation at break [%] | 2.1 | 2.2 | 2.1 | 2.4 | 2.4 | 2.4 | 2.2 |
| Impact resistance [kJ/m$^2$] | 40 | 41 | 39 | 48 | 48 | 47 | 47 |
| Notched impact resistance [kJ/m$^2$] | 6.3 | 6.6 | 6.2 | 7.7 | 7.5 | 7.6 | 7.5 |

*in dichloroacetic acid, pure PBT (uncompounded) gives 1450

The incorporation of DEPAL and MC and the further additives (examples C-4-6) leads only to a V-1 classification and distinct polymer degradation, evident from the low solution viscosities. The mechanical values are also low compared to non-flame-retardant PBT. The inventive combination of DEPAL with EPAL and optionally the further additives virtually completely suppressed polymer degradation; fire class V-0 is attained and the mechanical values are improved.

EXAMPLE 13

In the case of unsaturated polyester resins and the epoxy resins, a reinforcing material, for example a continuous glass textile mat of basis weight 200 g/m$^2$, is impregnated with a homogenized mixture (UP 1, EP 1) of resin, accelerator, the flame retardant component(s), hardener and possibly solvent, hardened at room temperature for 24 hours and heat-treated at 80° C. for an additional 3 hours.

UP 1:
100 parts Palatal® A 400-01 unsaturated polyester resin, 0.5 part NL-49 P, 70 parts EPAL/DEPAL, 2 parts Butanox M-50.

EP 1:
100 parts Beckopox EP 140, 41 parts Beckopox EH 628, 30 parts EPAL/DEPAL

The fire performance was tested by the Underwriters Laboratories method "Test for Flammability of Plastics Materials—UL 94" in the version dated Feb. 5, 1975 on test specimens of above-described laminates of length 127 mm, width 12.7 mm and thickness 1.6 mm.

The laminates obtained from mixtures UP 1, UP 2, EP 1 and EP 2 have a UL-94 classification which was determined to be V-0.

The invention claimed is:

1. A process for preparing mixtures of alkylphosphonous salts and dialkylphosphinic salts, comprising the steps of:
    a) reacting a phosphinic acid source (I)

with ethylene
in the presence of a catalyst A to give a mixture of alkylphosphonous acid (III) and dialkylphosphinic acid (IV) or salts or esters thereof

where R$^1$, R$^2$, R$^3$, R$^4$ are each H, and A and B are each ethyl and X is H, Mg, Ca, Ba, Al, Pb, Fe, Zn, Mn, Ni, Li, Na, K, where m is ⅓, ½, 1, and the catalyst A is a free-radical initiator and b) reacting the mixture of alkylohosphonous acid (III) and dialkylphosphinic acid (IV) or salts or esters thereof with metal compounds of Mg, Ca, Al, Sb, Sn, Ge, Ti, Fe, Zr, Zn, Ce, Bi, Sr, Mn, Li, Na, K to give the mixtures of alkylphosphonous salt (V) and dialkylphosphinic salt (VI) of these metals, or a combination thereof

where A and B are each ethyl and Y is Mg, Ca, Al, Sb, Sn, Ge, Ti, Fe, Zr, Zn, Ce, Bi, Sr, Mn, Li, Na, K, or a combination thereof and n is ¼, ⅓, ½, 1 and wherein the mixture of alkylphosphonous salt (V) and dialkylphosphinic salt (VI) comprises 3 to 30% by weight of alkylphosphonous salt (V) and 70 to 97% by weight of dialkylphosphinic salt (VI).

2. The process as claimed in claim 1, wherein the phosphinic acid source (I) is selected from the group consisting of phosphinic acid, or the sodium, potassium, calcium, magnesium, aluminum, ammonium salt methyl, ethyl, propyl, i-propyl, butyl, t-butyl, glycol ester thereof and combinations thereof.

3. The process as claimed in claim 1, wherein the free-radical initiator is peroxomonosulfuric acid, potassium peroxomonosulfate, peroxodisulfuric acid, potassium peroxodisulfate, sodium peroxodisulfate, ammonium peroxodisulfate, hydrogen peroxide, performic acid, peracetic acid, dibenzoyl peroxide, di-tert-butyl peroxide, dicumyl peroxide, 2,4-dichlorobenzoyl peroxide, 2,2'-azobis[2-(2-imidazolin-2-yl)propane] dihydrochloride, 2,2'-azobis[2-(2-imidazolin-2-yl)propane]disulfate dihydrate, 2,2'-azobis(2-methylpropionamidine) dihydroohloride, 2,2'-azobis[2-(2-imidazolin-2-yl)propanel], 2,2'-azobis(1-imino-1-pyrrolidino-2-ethylpropane) dihydrochloride, 4,4'-azobis(4-cyanopentanoic acid) 2,2'-azobis(2,4-dimethylvaleronitrile), azobis(isobutyronitrile), 2,2'-azobis(2-metnylbutyronitrile), dimethyl 2,2'-azobis(2-methylpropionate), 1,1'-azobis(cyclohexane-1-carbonitrile), or a combination thereof.

4. The process as claimed in claim 1, wherein the mixture of alkylphosphonous salts and dialkylphosphinic salts comprises, based on the total weight of the mixture, 0 to 5% by weight of alkylohosphonic salts, telomeric dialkylphosphinic salts or a combination thereof.

5. A flame retardant or as an intermediate for preparation of flame retardants for thermoplastic polymers, for thermoset polymers, for clearcoats, for intumescent coatings, for wood and other cellulosic products, for production of flame-retardant polymer molding compositions, for production of flame-retardant polymer moldings and/or for rendering pure and blended polyester and cellulose fabrics flame-retardant by impregnation comprising a mixture of alkylphosphonous salts and dialkylphosphinic salts prepared in accordance with the process of claim 1.

6. The flame retardant or intermediate as claimed in claim 5, wherein the thermoplastic polymers are polyester, polystyrene, polyamide or a combination thereof, and the thermoset polymers are unsaturated polyester resins, epoxy resins, polyurethanes, acrylates or a combination thereof.

7. The flame retardant or intermediate as claimed in claim 5, wherein the mixture of alkylphosphonous salts and dialkylphosphinic salts comprises 0.5 to 35% by weight of alkylphosphonous salt and 65 to 99.5% by weight of dialkylphosphinic salt.

8. A flame-retardant thermoplastic or thermoset polymer molding composition comprising 2 to 50% by weight of a mixture of alkylphosphonous salts and dialkylphosphinic salts prepared according to the process of claim 1, based on the thermoplastic or thermoset polymer.

9. A flame-retardant thermoplastic or thermoset polymer molding, film, filament or fiber comprising 2 to 50% by weight of a mixture of alkylphosphonous salts and dialkylphosphinic salts prepared according to the process of claim 1, based on the thermoplastic or thermoset polymer.

10. A flame-retardant thermoplastic or thermoset polymer molding, film, filament or fiber comprising 3 to 40% by weight of a mixture of alkylphosphonous salts and dialkylphosphinic salts prepared according to the process of claim 1 based on the thermoplastic or thermoset polymer.

* * * * *